United States Patent
Devgon

(10) Patent No.: US 8,366,685 B2
(45) Date of Patent: *Feb. 5, 2013

(54) SYSTEMS AND METHODS FOR PHLEBOTOMY THROUGH A PERIPHERAL IV CATHETER

(75) Inventor: Pitamber Devgon, Philadelphia, PA (US)

(73) Assignee: Creative Vascular, LLC, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/456,900

(22) Filed: Apr. 26, 2012

(65) Prior Publication Data
US 2012/0277627 A1  Nov. 1, 2012

Related U.S. Application Data

(63) Continuation-in-part of application No. 13/234,857, filed on Sep. 16, 2011.

(60) Provisional application No. 61/479,223, filed on Apr. 26, 2011.

(51) Int. Cl.
*A61B 10/00* (2006.01)
*B65D 81/00* (2006.01)
*A61M 5/00* (2006.01)

(52) U.S. Cl. ........ 604/263; 604/173; 604/175; 604/246; 604/256; 604/264; 600/573; 600/575; 600/576; 600/578; 600/579

(58) Field of Classification Search .................. 600/573, 600/575, 576, 578, 579; 604/164.07, 164.12, 604/173, 175, 246, 256, 263
See application file for complete search history.

(56) References Cited

U.S. PATENT DOCUMENTS

| | | | |
|---|---|---|---|
| 4,192,319 | A | 3/1980 | Hargens et al. |
| 4,808,158 | A | 2/1989 | Kreuzer et al. |
| 5,147,334 | A | 9/1992 | Moss |
| 5,201,722 | A | 4/1993 | Moorehead et al. |
| 5,203,771 | A | 4/1993 | Melker et al. |
| 5,360,407 | A | 11/1994 | Leonard |
| 5,562,631 | A | 10/1996 | Bogert |
| 5,611,782 | A | 3/1997 | Haedt |
| D384,741 | S | 10/1997 | Musgrave et al. |
| 5,749,857 | A | 5/1998 | Cuppy |
| 5,755,709 | A | 5/1998 | Cuppy |
| 5,853,393 | A | 12/1998 | Bogert |
| 5,944,695 | A | 8/1999 | Johnson et al. |
| 6,080,138 | A | 6/2000 | Lemke et al. |
| 6,197,001 | B1 | 3/2001 | Wilson et al. |

(Continued)

FOREIGN PATENT DOCUMENTS
WO    WO 2011/011436 A2    1/2011

OTHER PUBLICATIONS

Himberger Jr., "Accuracy of drawing blood through infusing intravenous lines," 2001 [retrieved on Mar. 16, 2011] Retrieved from the Internet <URL: <http://www.ncbi.nlm.nih.gov/pubmed/?term=Accuracy%20of%20drawing%20blood%20through%20infusing%20intravenous%20lines>.

(Continued)

*Primary Examiner* — Sean Dougherty
(74) *Attorney, Agent, or Firm* — Cooley LLP

(57) ABSTRACT

An apparatus for performing phlebotomy through a peripheral intravenous line is described herein. The apparatus includes an introducer and a cannula and is configured to advance the cannula through a peripheral intravenous line. A y-adapter with a port of larger diameter is configured to receive the cannula to place the cannula in fluid communication with the peripheral intravenous line. When advanced, the cannula is configured to transport a bodily fluid to a volume outside of the body.

21 Claims, 29 Drawing Sheets

U.S. PATENT DOCUMENTS

| | | | |
|---|---|---|---|
| 6,692,473 | B2 | 2/2004 | St. Cyr et al. |
| 6,719,726 | B2 | 4/2004 | Meng et al. |
| 6,719,781 | B1 | 4/2004 | Kim |
| 6,908,459 | B2 | 6/2005 | Harding et al. |
| 7,135,008 | B2 | 11/2006 | O'Mahony et al. |
| 7,252,654 | B2 | 8/2007 | VanTassel et al. |
| 7,311,689 | B2 | 12/2007 | Levin et al. |
| 7,462,161 | B2 | 12/2008 | O'Mahony et al. |
| 7,615,033 | B2 | 11/2009 | Leong |
| 7,670,320 | B2 * | 3/2010 | Iwase et al. ........... 604/198 |
| 7,691,088 | B2 | 4/2010 | Howell |
| 7,713,250 | B2 | 5/2010 | Harding et al. |
| 7,717,882 | B2 | 5/2010 | Harding |
| 7,762,977 | B2 | 7/2010 | Porter et al. |
| 7,766,961 | B2 | 8/2010 | Patel et al. |
| 7,771,394 | B2 | 8/2010 | Shue et al. |
| 2002/0120215 | A1 | 8/2002 | Crawford et al. |
| 2004/0138622 | A1 | 7/2004 | Palasis |
| 2004/0181192 | A1 | 9/2004 | Cuppy |
| 2007/0219460 | A1 * | 9/2007 | Goldenberg ........... 600/566 |
| 2007/0282280 | A1 | 12/2007 | Tennican |
| 2008/0045862 | A1 | 2/2008 | Dalebout et al. |
| 2009/0156963 | A1 | 6/2009 | Noble et al. |
| 2010/0286657 | A1 | 11/2010 | Heck |
| 2010/0305519 | A1 | 12/2010 | McKennon et al. |
| 2012/0191010 | A1 | 7/2012 | Cabot |

OTHER PUBLICATIONS

Cox, et al. "Blood Samples Drawn from IV Catheters Have Less Hemolysis When 5-mL (vs 10-mL) Collection Tubes Are Used," 2004 [retrieved on Mar. 16, 2011] Retrieved from the Internet <URL: http://www.jenonline.org/article/S0099-1767(04)00634-8/fulltext>, 2 pgs.

Jagger, et al., "Drawing Venous Blood With Syringes: A Risky Use of Injection Equipment," Advances in Exposure Prevention, vol. 5, No. 3, 2000, 3 pgs.

Who guidelines on drawing blood: best practices in phlebotomy, © World Health Organization 2010, 125 pgs.

"Connect and Protect with BD Diagnostics—Preanalytical Systems," BD Vacutainer®, Luer-Lok™, Access Device, 2 pgs.

"Needleless IV Access Devices," BD Q-Syte™, Luer Access Split-Septum, 2007, 1 pg.

"Evidence-Based Practice (EBP) Guideline Drawing Labs from Peripheral IV Sites," Nursing Research Council of United Hospital—Developed Apr. 2004; Revised Mar. 2009, 3 pgs.

Frey, "Drawing Blood Samples From Vascular Access Devices: Evidence-based Practice," Journal of Infusion Nursing: Sep./Oct. 2003, vol. 26, Issue 5, pp. 285-293, Article: CE, Abstract, [retrieved on Mar. 16, 2011], 1 pg.

"Blood Sampling Hemolysis Study for the MaxPlus™ Positive Flow Connector," Maximus Medical Products, Inc. © 2003, 1 pg.

"Vascular Access Procedures," Vascular Access Procedures, [retrieved on Mar. 16, 2011] Retrieved from the Internet <URL: http://www.radiologyinfo.org/en/info.cfm?pg=vasc_access> 7 pgs.

* cited by examiner

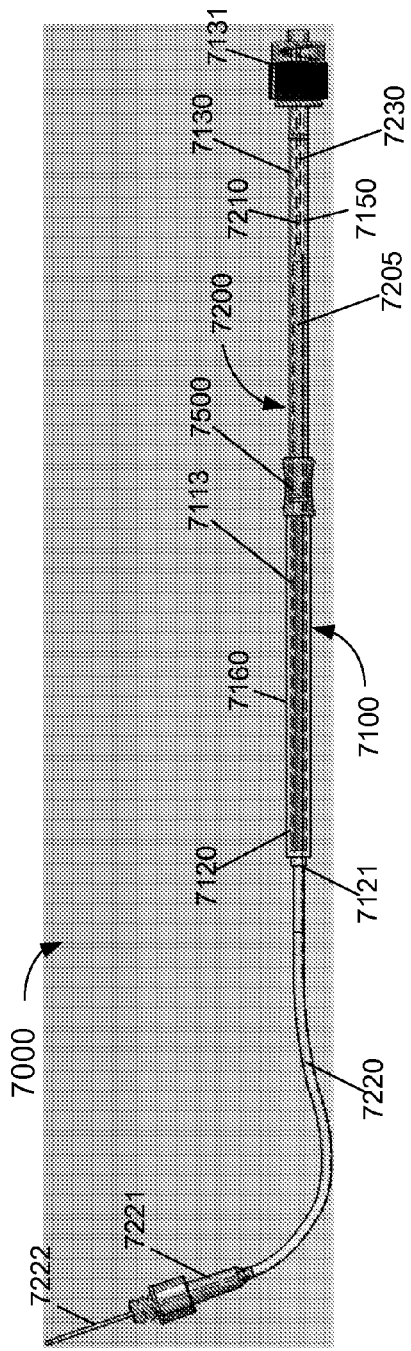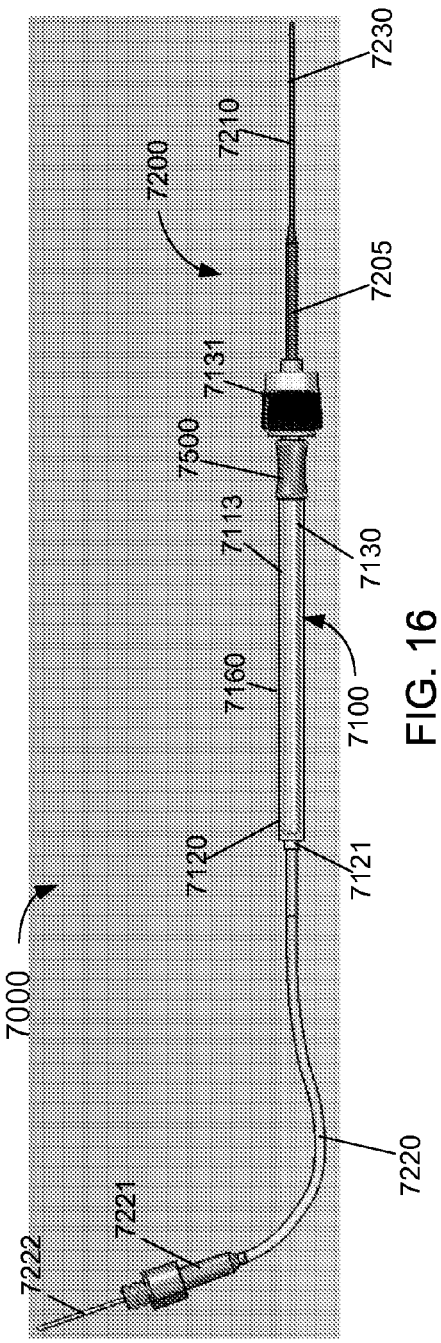
FIG. 15
FIG. 16

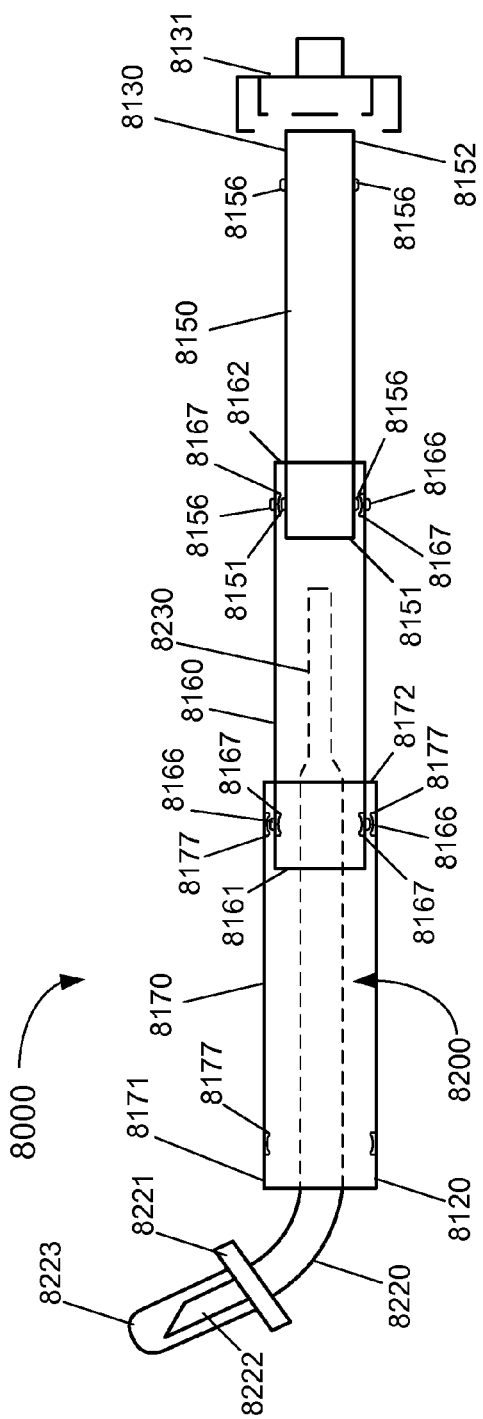
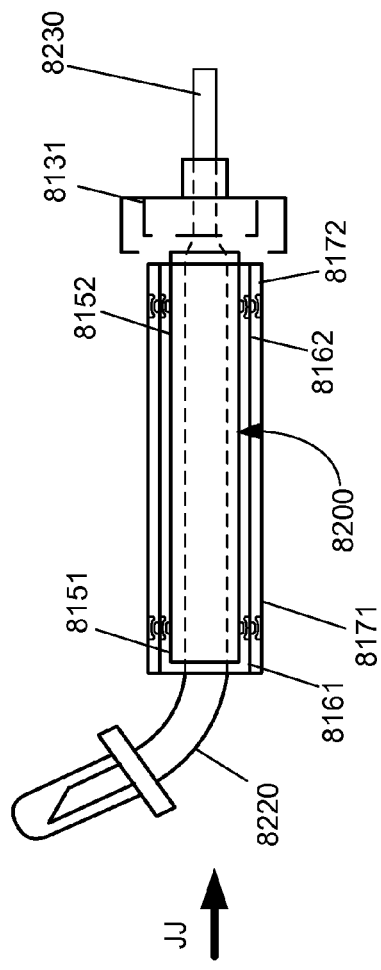

SYSTEMS AND METHODS FOR PHLEBOTOMY THROUGH A PERIPHERAL IV CATHETER

CROSS-REFERENCE TO RELATED APPLICATIONS

This application is a continuation-in-part of U.S. application Ser. No. 13/234,857 entitled "Systems and Methods for Phlebotomy Through a Peripheral IV Catheter," filed on Sep. 16, 2011, which claims priority under 35 U.S.C. 119(e) to U.S. Provisional Application Ser. No. 61/479,223 entitled "Systems and Methods for Phlebotomy Through a Peripheral IV Catheter," filed on Apr. 26, 2011, each of which is incorporated herein by reference in its entirety.

BACKGROUND

The embodiments described herein relate generally to medical devices. More particularly, the embodiments described herein relate to systems and methods for phlebotomy through an intravenous catheter.

The typical hospitalized patient encounters a needle every time a doctor orders a lab test. The standard procedure for blood extraction involves using a metal needle ("butterfly needle") to "stick" patients' veins in their arms or hands. Blood drawing is a manual, labor-intensive process, with the average patient requiring hours of direct skilled labor during a typical hospital stay. This needle stick is not only painful and a major source of patient dissatisfaction, but the nurses or specialized blood drawing personnel (phlebotomists) often have difficulty finding the vein in approximately 10-15% of patients, resulting in multiple, painful "stick" attempts. This results in significantly higher material and labor costs (needles and tubing must be disposed of after every attempt) and increased patient pain and bruising.

The current process for drawing blood is inefficient, taking on average 7-10 minutes, and more than 21 minutes for 10% of patients. These 10% of patients are referred to as Difficult Intra-Venous Access or more commonly as "tough stick" patients. If superficial veins are not readily apparent, blood can be forced into the vein by massaging the arm from wrist to elbow, tapping the site with the index and middle finger, applying a warm, damp washcloth to the site for 5 minutes, or by lowering the extremity over the bedside to allow the veins to fill. Each of these methods is time consuming and therefore costly.

Peripheral IV catheters (PIVs) are inserted into most patients while they are hospitalized and used for infusing fluids and medications. However, they are not designed for blood extractions. The failure rates for aspiration reach 20-50% when PIVs have been left inserted for more than a day. Blood extracted from PIVs is often hemolyzed (e.g., defined as the rupture of red blood cells and the release of their contents into surrounding fluid) resulting in a discarded sample and the need to repeat the blood collection.

There are several mechanical barriers that can contribute to the shortcomings of extracting blood from a PIV. First, most catheters are formed from a soft bio-reactive polymer, the use of this material has led to a potential narrowing or collapse of the catheter as the negative pressure is applied for aspiration or the catheter is kinked during insertion or manipulation, preventing backflow. Additionally, with longer indwelling times comes an increase in debris (e.g., fibrin/platelet clots) that build up on the tip of the catheter and within the lumen. This explains the relationship between failure rate and indwelling time. A third significant barrier is attributed to a "suction cup" effect, wherein the negative pressure created by aspiration through the catheter and the possible curved path of a vein result in the tip of the catheter adhering to the wall of the vein. As the negative pressure increases the vein can rupture resulting in "blowing the vein," a major concern for phlebotomists during aspiration through a PIV.

Thus, a need exists for an improved system and method for phlebotomy through a peripheral intravenous catheter.

SUMMARY

Systems and methods for phlebotomy through a peripheral intravenous catheter are described herein. In some embodiments, an apparatus includes a cannula or catheter, an introducer, a locking mechanism, and an actuator. The cannula includes a proximal end and a distal end and defines a lumen. The introducer includes a proximal end and a distal end and defines a lumen configured to receive at least a portion of the cannula. The locking mechanism is coupled to the distal end of the introducer and is configured to couple the introducer to a peripheral intravenous line. The actuator is operatively coupled to the cannula and is configured to move the cannula between a first configuration, in which the cannula is substantially within the introducer, and a second configuration, in which the cannula is substantially outside the introducer. The cannula extends past an end of the peripheral intravenous line when in the second configuration.

BRIEF DESCRIPTION OF THE DRAWINGS

FIGS. 15 and 16 are a side view of an apparatus in a first configuration and a second configuration, respectively, according to an embodiment.

FIGS. 23 and 24 are schematic illustrations of an apparatus in a first configuration and a second configuration, according to an embodiment.

DETAILED DESCRIPTION

Figure 1:
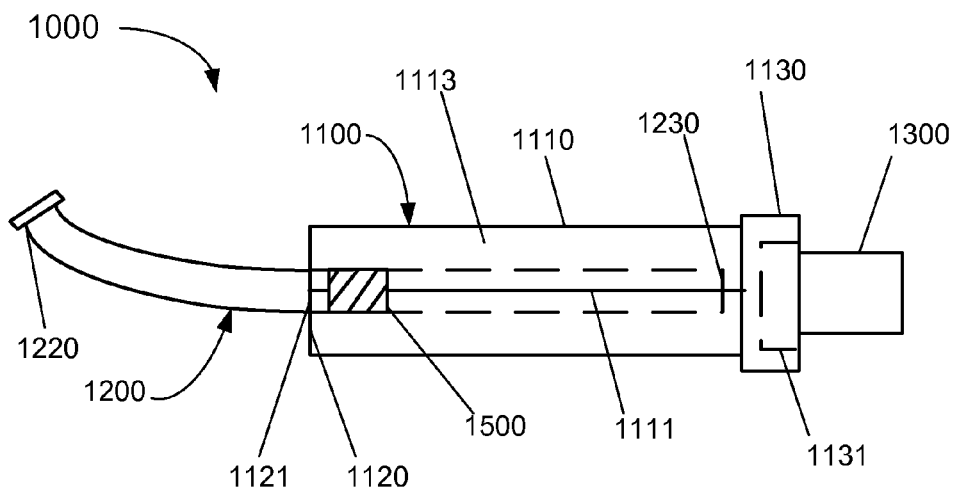
FIGS. 1 and 2 are schematic illustrations of an apparatus in a first configuration and a second configuration, respectively, according to an embodiment.

Systems and methods for phlebotomy through a peripheral intravenous catheter are described herein. In some embodiments, an apparatus includes a cannula or catheter, an introducer, a locking mechanism, and an actuator. The catheter includes a proximal end and a distal end and defines a lumen. The introducer includes a proximal end and a distal end and defines a lumen configured to receive at least a portion of the catheter. The locking mechanism is coupled to the distal end of the introducer and is configured to couple the introducer to a peripheral intravenous line. The actuator is operatively coupled to the catheter and is configured to move the catheter between a first configuration, in which the catheter is substantially within the introducer, and a second configuration, in which the catheter is substantially outside the introducer. The catheter extends past an end of the peripheral intravenous line when in the second configuration.

In some embodiments, a method includes coupling an introducer to a peripheral intravenous line (e.g., saline locked device, heparin locked device, or the like), the introducer having a proximal end and a distal end. The method further includes advancing a catheter from a first position inside the introducer and outside the peripheral intravenous line to a second position substantially outside the introducer and inside the peripheral intravenous line. In some embodiments, the catheter has a length greater than a length of the peripheral intravenous line, while in other embodiments, the catheter, in the second position, is shorter than the peripheral intravenous line. The method includes coupling a container to the proximal end of the introducer such that the container is fluidically coupled to the catheter. The method further includes withdrawing the catheter from the second position to the first position.

In some embodiments, a catheter has a proximal end and a distal end and defines a lumen therethrough. An introducer has a proximal end and a distal end and defines a lumen therethrough. The introducer is configured to receive the catheter therein. An adapter is coupled to the introducer. The adapter has a distal end configured to be coupled to a peripheral intravenous line. The adapter defines a first lumen and a second lumen. The first lumen has a first diameter and is configured to receive the catheter therethrough. The second lumen is orthogonal to the first lumen. An actuator is operatively coupled to the catheter and is configured to move the catheter between a first configuration and a second configuration. The catheter extends past the distal end of the adapter in the second configuration.

As used herein, the terms "catheter" and "cannula" are used interchangeably to define an element configured to define a passageway for moving a bodily fluid from a first location to a second location (e.g., a fluid passageway to move a bodily fluid out of the body). While cannulas can be configured to receive a trocar, a guide wire, or an introducer to deliver the cannula to a volume inside the body of a patient, the cannulas referred to herein need not include or receive a trocar, guide wire, or introducer.

As used in this specification, the terms "Y-adapter" and "T-adapter" are used to refer to a dual port IV extension set. In this manner, the terms "Y-adapter" and "T-adapter" generally describe an overall shape of the dual port IV extension set. For example, as used herein, a Y-adapter is substantially "Y" shaped including a single port at a first end and two ports angularly disposed at a second end. Furthermore, the terms "Y-adapter" and "T-adapter" are included by way of example only and not limitation. For example, in some embodiments, an apparatus can include a single port IV extension set (e.g., a single port adapter) or a multi port IV extension set (e.g., an adapter with more than two ports).

As used in this specification, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the term "stiffness" relates to an object's resistance to deflection, deformation, and/or displacement by an applied force. Stiffness can be characterized in terms of the amount of force applied to the object and the resulting distance through which a first portion of the object deflects, deforms, and/or displaces with respect to a second portion of the object. When characterizing the stiffness of an object, the deflected distance may be measured as the deflection of a portion of the object different from the portion of the object to which the force is directly applied. Said another way, in some objects, the point of deflection is distinct from the point where force is applied.

Stiffness is an extensive property of the object being described, and thus is dependent upon the material from which the object is formed as well as certain physical characteristics of the object (e.g., shape and boundary conditions). For example, the stiffness of an object can be increased or decreased by selectively including in the object a material having a desired modulus of elasticity, flexural modulus, and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the stiffness of the object can be increased, for example, by introducing into the object and/or constructing the object of a material having a high modulus of elasticity.

Similarly, a material's hardness is an intensive property of the constituent material and describes the measure of how resistant the material is to various kinds of permanent shape change when a force is applied. In discussing the hardness and the subsequent effect on the stiffness of a catheter, the Shore durometer scale is generally used. There are several scales for durometers with two commonly used in describing plastics, polymers, elastomers, and/or rubbers, namely, type A and type D, where type A is generally used for softer materials and type D is generally used for harder materials. The Shore durometer of a material is denoted by a number between 0 and 100, with higher numbers indicating a harder material, followed by the type of scale. For instance, a first material can be measured as having a Shore durometer of 40 Shore A and a second material can be measured as having a Shore durometer of 60 Shore D. Therefore, according to the Shore durometer scale, the second material is harder and thus, more stiff than the first material.

Figure 2:
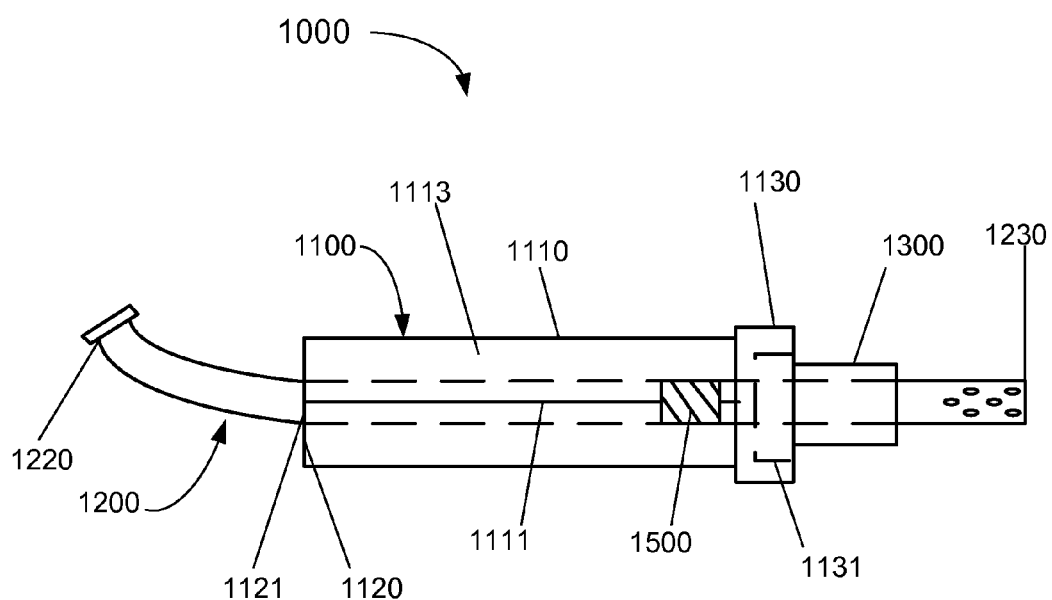

FIGS. 1 and 2 are schematic illustrations of an apparatus 1000 for phlebotomy through a peripheral intravenous line or catheter in a first configuration and second configuration, respectively, according to an embodiment. The apparatus 1000 includes an introducer 1100, a cannula or catheter 1200, a lock mechanism 1131, and an actuator 1500. The introducer 1100 includes a sheath 1110 having a proximal end 1120 and a distal end 1130 and defining a lumen 1113. The catheter/cannula 1200 is movably disposed within sheath 1110 between the proximal end 1120 and the distal end 1130.

The proximal end 1120 includes a port 1121, such that the catheter/cannula 1200 can move from the first, retracted configuration (FIG. 1) to the second, extended configuration (FIG. 2). Similarly stated, the port 1121 at the proximal end 1120 of the introducer 1100 is configured such that the catheter 1200 may move through the port 1121 from the first configuration to the second configuration. The port 1121 can be any suitable port such as, for example, an opening in the proximal end 1120 of the introducer 1100. Furthermore, the port 1121 can include any suitable seal member such as an o-ring or a gasket. In some embodiments, the port 1121 can be a self-sealing port and can be lubricated using any suitable lubrication to aid in the movement and/or sealing of the catheter 1200 therein.

The distal end 1130 of the introducer 1100 includes a locking mechanism 1131 configured to fluidically couple a peripheral intravenous line 1300 to the introducer 1100 and place the catheter 1200 into fluid communication with the peripheral intravenous line 1300. The locking mechanism 1131 can be any suitable locking mechanism that creates a fluid-tight seal. In some embodiments, the locking mechanism can be a Luer lock or similar configuration. In some embodiments, the peripheral intravenous line 1300 is in a sealed configuration until the locking mechanism 1131 is coupled to the intravenous line 1300. Once the locking mechanism 1131 is coupled to the intravenous line 1300, the seal can be opened to allow access for the catheter 1200. In some embodiments, the locking mechanism can include a back flow prevention mechanism such as a one way valve or the like. In this manner, the lock mechanism 1131 can be configured to allow the catheter 1200 to pass through the lock mechanism 1131 but substantially prevent a fluid flow, outside the catheter 1200, through the lock mechanism 1131.

The catheter 1200 defines a lumen 1201 between a proximal end 1220 and a distal end 1230 and may be any suitable diameter and stiffness. In some embodiments, the catheter 1200 can be between a 16-gauge and 26-gauge and have a Shore durometer of approximately 20 Shore A to 50 Shore D. In some embodiments, the catheter 1200 has a Shore durometer of approximately 20 Shore A to 95 Shore D. In some embodiments, the catheter 1200 has a Shore durometer of approximately 70 Shore D to 85 Shore D. In this manner, the catheter 1200 can be any suitable diameter to be inserted through the peripheral intravenous line 1300 and can be sufficiently stiff to be advanced through the peripheral intravenous line 1300.

The actuator 1500 is operatively coupled to the catheter 1200 through a groove or slot 1111 in the introducer 1100. The actuator 1500 is configured to move the catheter 1200 from the first configuration to the second configuration such that the distal end 1230 of the catheter 1200 is substantially outside the introducer 1100, as shown in FIG. 2. In some embodiments, the length of the distal end 1230 of the catheter 1200 is greater than the length of the peripheral intravenous line 1300. In this manner, the distal end 1230 of the catheter 1200 extends past the distal end of the intravenous line 1300.

In some embodiments, the catheter 1200 can be moved to a third configuration in which the catheter 1200 is retracted back into the introducer 1100. The third configuration can be substantially similar to the first configuration (FIG. 1) in that the catheter 1200 is positioned in the introducer 1100, thus, the user does not come into contact with bodily fluids. While in the first configuration and the third configuration, the apparatus 1000 can be disconnected from or connected to a peripheral intravenous line 1300. Said another way, the apparatus 1000 can be in the first configuration before it is coupled to the peripheral intravenous line 1300, then remain in the first configuration for a period of time after being coupled to the peripheral intravenous line 1300. Similarly, the apparatus 1000 can be moved to the third configuration, be disconnected from the peripheral intravenous line 1300, and then remain in the third configuration.

Figure 3:
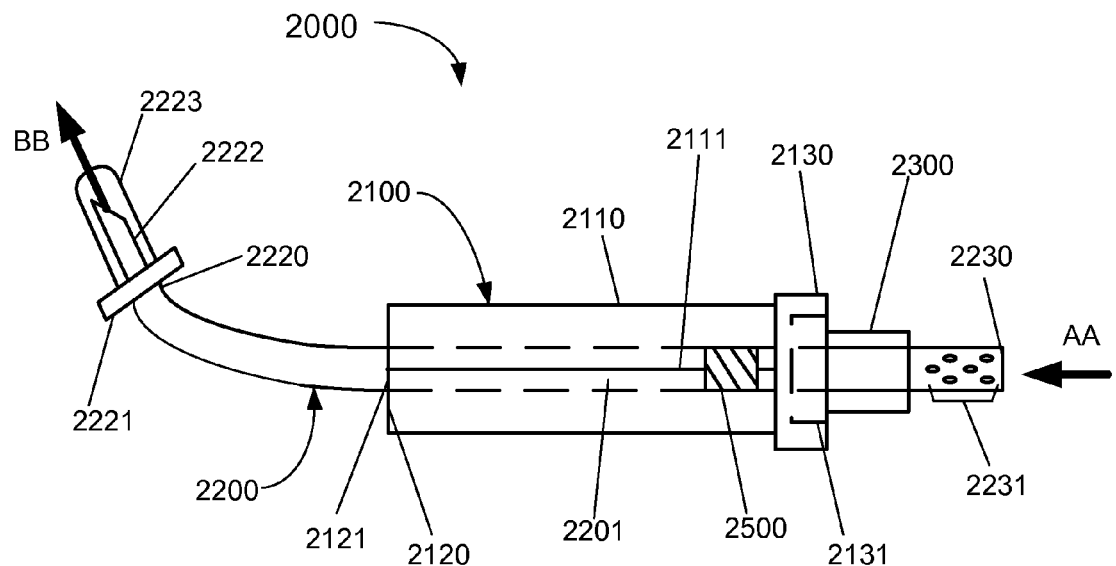
FIG. 3 is a detailed schematic illustration of an apparatus in a second configuration, according to an embodiment.

FIG. 3 is a detailed schematic illustration of an apparatus 2000 according to an embodiment in a second configuration. In some embodiments, the apparatus 2000 is substantially similar to the apparatus 1000 described above in reference to FIGS. 1 and 2. Therefore, aspects of the apparatus 2000 are not described in detail herein. The apparatus 2000 includes an introducer 2100 and a catheter 2200. The catheter 2200 includes a proximal end 2220 and a distal end 2230. The distal end 2230 of the catheter 2200 includes a set of openings 2231 such that when in the second configuration (e.g., when the distal end 2230 of the catheter 2200 is in the vein and outside the intravenous line) the openings 2231 act to transport a bodily fluid (e.g., blood) to a volume outside the catheter 2200. The set of openings 2231 can be of any arrangement on the circumference of the catheter 2200 and can include the end of the catheter 2200. Similarly stated, the catheter 2200 having the distal end 2230 can define an opening at the tip surface. Each opening 2231 can be of any suitable shape or size and are not necessarily similar to any other opening included in the set of openings 2231. In some embodiments, the catheter 2200 defines a single opening. For example, in some embodiments, the catheter 2200 defines a single opening 2231 at the distal surface.

The proximal end 2220 of the catheter 2200 is fluidically coupled to a locking mechanism 2221, as shown in FIG. 3. The locking mechanism 2221 can be any suitable locking mechanism such as a Luer lock or the like. A needle 2222 is fluidically coupled to the locking mechanism 2221 and at least partially disposed within a sheath 2223. The sheath 2223 can be any material with a suitable flexibility and/or compressibility such that the needle 2222 can extend through the sheath 2223 when engaged with a conventional phlebotomy fluid container (e.g., a Vacutainer®). The locking mechanism 2221 is configured to be coupled to any suitable fluid containment system such as a Vacutainer® holder (not shown in FIG. 3) and place the needle 2222 in fluid communication with the fluid containment system. The sheath 2223 is configured to compress when the locking mechanism 2221 is coupled to the fluid containment system. This arrangement facilitates the passage of bodily fluids through the set of openings 2231 of the catheter 2200, as shown in FIG. 3 by arrow AA, through the catheter 2200, and exiting the catheter 2200 through the needle 2222, as shown in FIG. 3 by arrow BB.

Figure 4:
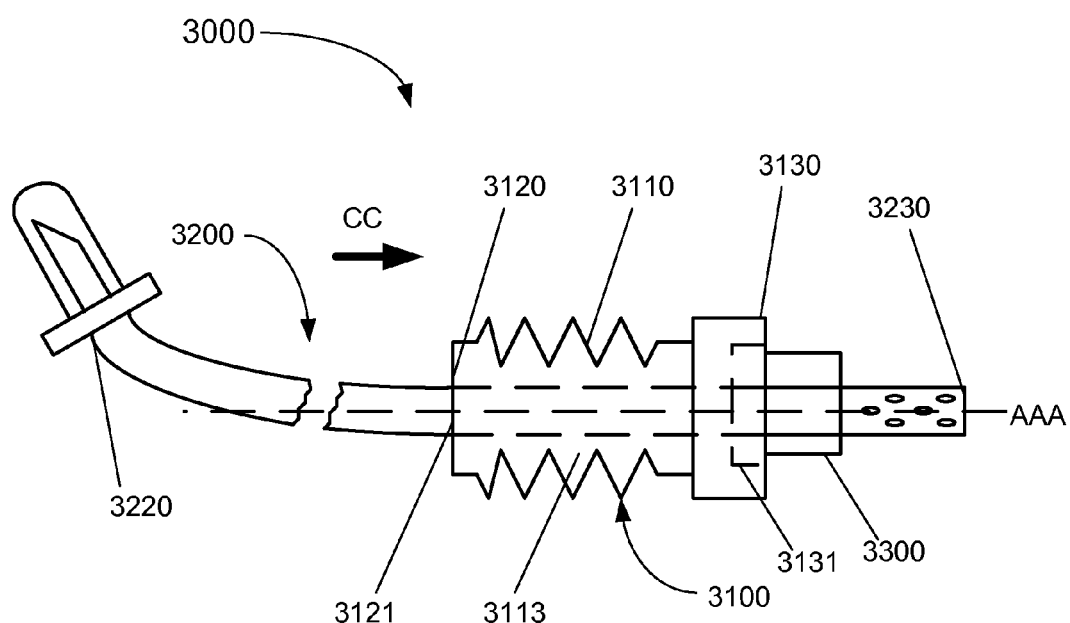
FIG. 4 is a detailed schematic illustration of an apparatus in a second configuration, according to an embodiment.

FIG. 4 is a schematic illustration of an apparatus 3000 for phlebotomy through a peripheral intravenous catheter in a second configuration according to an embodiment. The apparatus 3000 includes an introducer 3100 and a catheter 3200. The introducer 3100 includes a sheath 3110 defining a lumen 3113 between a proximal end 3120 and a distal end 3130 and configured to house, at least partially, the catheter 3200. The distal end 3130 of the introducer 3100 includes a locking mechanism 3131 configured to fluidically couple the introducer 3100 to a peripheral intravenous line 3300 and place the catheter 3200 into fluid communication with the peripheral intravenous line 3300, when the catheter 3200 is in the second configuration. The locking mechanism 3131 can be any suitable locking mechanism that creates a fluid-tight seal. In some embodiments, the locking mechanism 3131 can be a Luer lock or similar configuration. The sheath 3110, having a given stiffness, is configured such that when applying a force to the proximal end 3120 (as indicated by the arrow CC in FIG. 4), the sheath 3110 compresses along an axis AAA.

The compression of the sheath 3110 is such that the catheter 3200 is advanced to the second configuration. Said another way, as the sheath 3110 of the introducer 3100 is compressed, the catheter 3200 moves from a first configuration where in the catheter 3200 is disposed within the introducer 3100 (as described above with respect to FIG. 1) to a second configuration wherein the distal end 3230 is substantially outside the introducer 3100, as shown in FIG. 4. Furthermore, the stiffness of the sheath 3110 is an extensive property and as such can have a set of properties (i.e. material, thickness, shape and/or the like) to allow the sheath 3110 to compress along the axis AAA with the desired amount of force applied at the proximal end 3120 of the introducer 3100. The set of properties allow the sheath 3110 to elastically deform (i.e. non-permanently) such that when the force is no longer applied to the proximal end 3120 of the introducer 3100, the apparatus 3000 returns to the first configuration. In the second configuration, the distal end 3230 of the catheter 3200 extends past the distal end of the peripheral intravenous line 3300. This arrangement allows for the transport of a bodily fluid to a volume outside the catheter 3200 and when complete, the apparatus 3000 can be placed in a third configuration, substantially similar to the first configuration.

Figure 5:
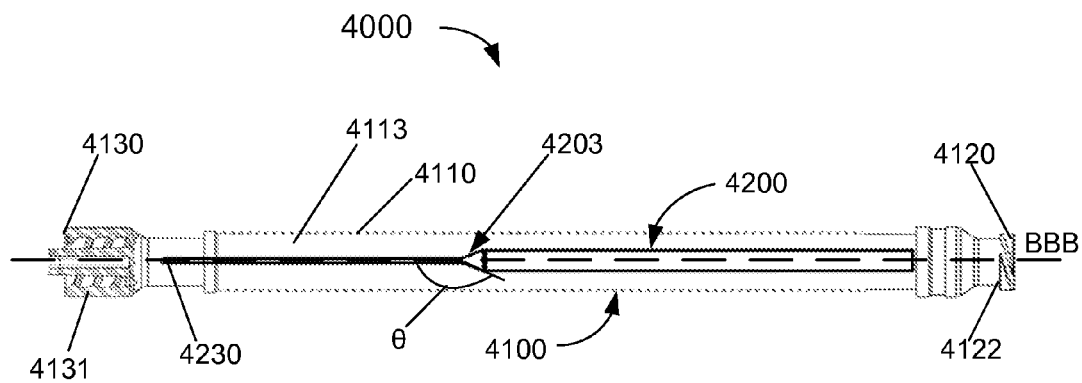
FIGS. 5 and 6 are cross-sectional side views of an apparatus in a first configuration and a second configuration, respectively, according to an embodiment.
Figure 6:
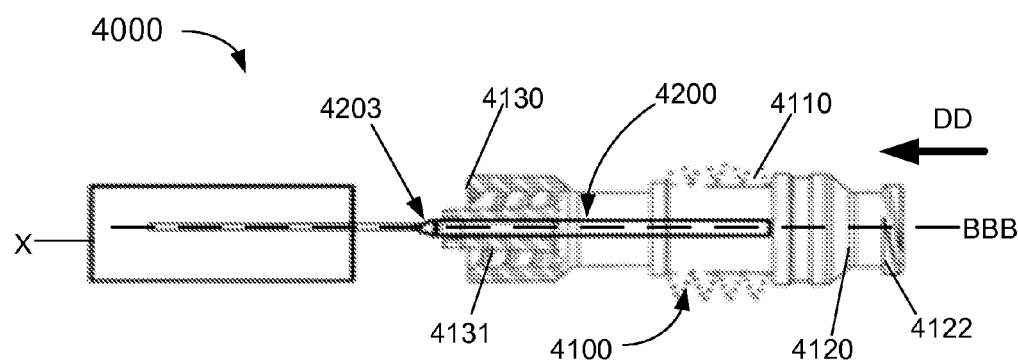

FIGS. 5 and 6 are side views of an apparatus 4000 according to an embodiment in a first configuration and a second configuration, respectively. The apparatus 4000 includes an introducer 4100 and a catheter 4200. The introducer 4100 includes a sheath 4110 defining a lumen 4113 between a proximal end 4120 and a distal end 4130 and is configured to house, at least partially, the catheter 4200. Although shown in FIG. 5 as being cylindrical, the introducer 4100 can be any suitable shape. Moreover, the lumen 4113, defined by the interior walls of the sheath 4110 is not necessarily the same shape as the exterior walls of the sheath 4110. Said a different way, the interior and exterior walls of the sheath 4110 can have a different cross sectional shape. The proximal end 4120 of the introducer 4100 is coupled to a locking mechanism 4122. The locking mechanism 4122 can be any suitable locking mechanism such as a Luer lock or the like. In use, the locking mechanism 4122 is configured to couple to a suitable fluid containment system such as a Vacutainer® holder (not shown in FIG. 5) to place the catheter 4200 in fluid communication with the fluid containment system.

The distal end 4130 of the introducer 4100 includes a locking mechanism 4131 configured to fluidically couple the introducer 4100 to a peripheral intravenous line (not shown in FIG. 5). In this manner, the locking mechanism 4131 can be configured to selectively place the catheter 4200 into fluid communication with the peripheral intravenous line. The locking mechanism 4131 can be any suitable locking mechanism that creates a fluid-tight seal. In some embodiments, the locking mechanism 4131 is in a sealed configuration until the locking mechanism 4131 is coupled to the intravenous line. Once the locking mechanism 4131 is coupled to the intravenous line, the seal can be opened to allow access for the catheter 4200. In addition, while in the unlocked configuration, the locking mechanism 4131 of the distal end 4130 and the locking mechanism 4122 of the proximal end 4120 create a fluidically isolated housing for the catheter 4200 therein. Stated similarly, prior to the proximal end locking mechanism 4122 and distal end locking mechanism 4131 being unlocked and before the catheter 4200 is in the second configuration, the catheter 4200 is sterile. Furthermore, the catheter 4200, when in the second configuration and having contacted the desired bodily fluid, can be moved to a third configuration (e.g., substantially similar to the first configuration) thereby isolating the used distal end 4230.

The sheath 4110 has a given stiffness such that when a force (as indicated by the arrow DD in FIG. 6) is applied to the proximal end 4120, the sheath 4110 compresses along an axis BBB. The compression of the sheath 4110 is such that the catheter 4200 is advanced to the second configuration. Said another way, as the sheath 4110 of the introducer 4100 is compressed, the catheter 4200 moves from the first configuration wherein the catheter 4200 is disposed within the introducer 4100 to the second configuration wherein the distal end 4230 is substantially outside the introducer 4100 (e.g., the sheath 4110 retracts). The properties of the sheath 4110 can be any set of properties discussed herein such that applying a desired amount of force to proximal end 4120 allows the sheath to compress along axis BBB. In the second configuration, the distal end 4230 of the catheter 4200 extends past the distal end of the peripheral intravenous line and allows for the transport of a bodily fluid to a volume outside of the catheter 4200.

Figure 6A:
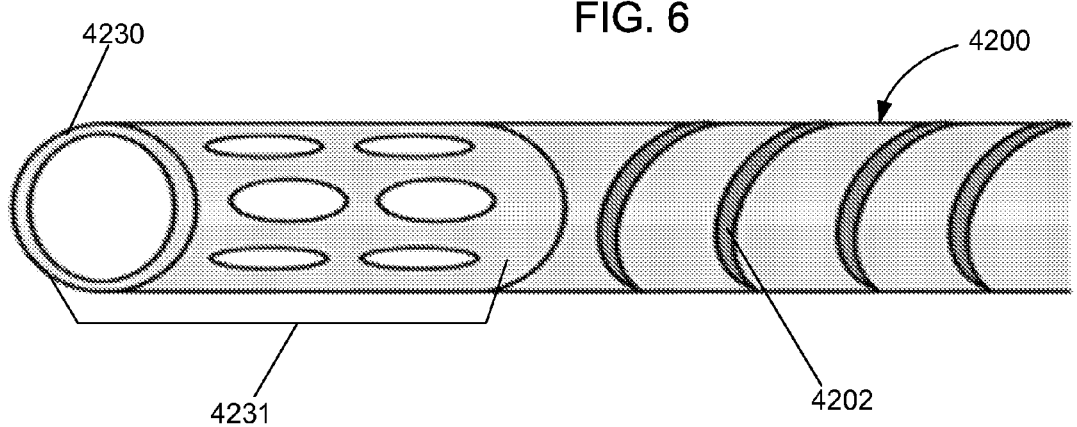
FIG. 6A is an enlarged view of a portion of the apparatus of FIG. 6, indicated by the region X.

The catheter 4200 includes a distal end 4230 and tapered portion 4203. The tapered portion is such that the diameter of the catheter 4200 is reduced at a given location, as shown in FIG. 5. The taper angle θ can be any suitable angle such that the catheter 4200 is allowed to advance fully to the second configuration (FIG. 6). Moreover, the taper angle θ is such that a laminar flow (i.e., smooth layered flow) is achieved. In some embodiments, the catheter 4200 can include a stiffening wire 4202, as shown in FIG. 6A, and can be configured to coil around the walls of the catheter 4200 providing the catheter 4200 with a desired stiffness. Moreover, the stiffening wire 4202, being coiled around the catheter 4200, can provide the flexibility to advance through a set of walls defining a lumen (i.e., veins, arteries, peripheral intravenous line, and/or the like) without kinking or binding. In addition, the stiffening wire 4202 can provide the catheter 4200 with enough stiffness to facilitate its advancement through the lumen.

The distal end 4230 of the catheter 4200 includes a set of openings 4231 such that when in the second configuration (e.g., when the distal end 4230 of the catheter 4200 is in the vein and outside the intravenous line) the openings 4231 act to transport a bodily fluid (i.e., blood) to a volume outside the catheter 4200. The set of openings 4231 can be of any arrangement on the circumference of the catheter 4200 and can include the end of the catheter 4200. Similarly stated, the catheter 4200 having the distal end 4230 can be substantially open at the tip surface. Although FIGS. 6 and 6A show the distal end 4230 of the catheter 4200 as substantially flat, the distal end 4230 may be any suitable shape, (e.g. conical or spherical) and can have any suitable degree of rounded edges. Each opening 4231 can be of any suitable shape or size and are not necessarily similar to any other opening 4231 included in the set of openings 4231. The arrangement of the set of openings 4231 is configured to introduce a laminar flow through catheter 4200 to a volume substantially outside the catheter 4200 and thus avoid hemolysis.

In some embodiments, a blood collection system consists of two elements: (1) the introducer/catheter blood collection assembly described above; and (2) a y-adapter that is configured to attach to a standard 16 g or 22 g peripheral IV catheter. The y-adapter includes a dedicated port for the blood collection device and another standard port for conventional medicine and fluid infusion.

Figure 7:
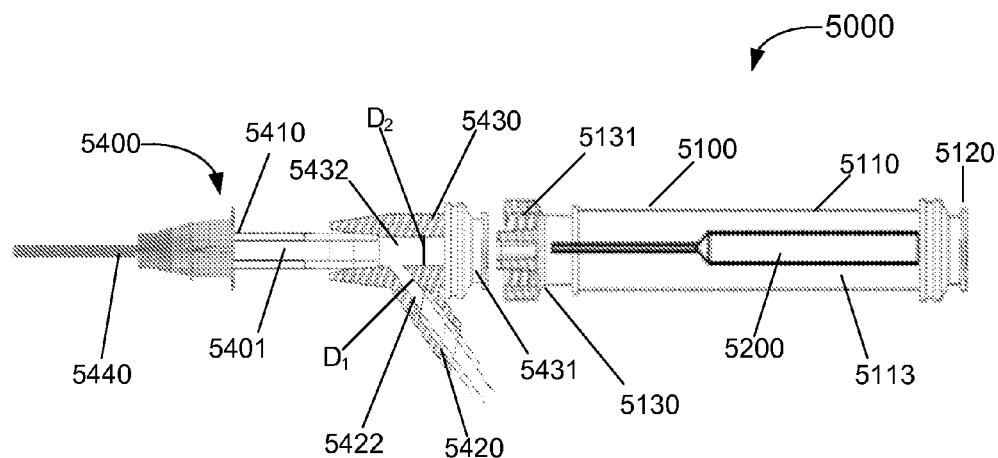
FIGS. 7 and 8 are cross-sectional side views of an apparatus and an adapter in a first configuration and a second configuration, respectively, according to an embodiment.

For example, FIG. 7 includes a cross-sectional view of a y-adapter 5400 and an apparatus 5000 in a first configuration, according to an embodiment. The apparatus 5000 includes an introducer 5100 and a catheter 5200. The introducer 5100 includes a sheath 5110 defining a lumen 5113 between a proximal end 5120 and a distal end 5130 and configured to house, at least partially, the catheter 5200. The catheter 5200 includes a proximal end 5220 and a distal end 5230. The apparatus 5000 can be substantially similar to the apparatus 4000 described above with reference to FIGS. 5 and 6. Therefore, aspects of the apparatus 5000 are not described in further detail herein.

In some embodiments, the y-adapter 5400 is configured to be coupled between the introducer 5100 and intravenous line 5440. The y-adapter includes a distal end 5410 and defines a first port 5420 and a second port 5430. The first port 5420 of the y-adapter 5400 defines a first lumen 5422 with a first diameter $D_1$. The first port 5420 is configured such that the first port 5420 is substantially similar in size, shape, configuration, and functionality of a conventional y-adapter. Moreover, the first port 5420 is configured such that the backflow of a bodily fluid cannot exit the first port 5420. More specifically, the first lumen 5422 defined by the walls of the first port 5420 can be such that the lumen 5422 restricts the backflow of a bodily fluid (i.e. blood). In some embodiments, the backflow can be prevented using a valve, screw cap, flip cap, port, and/or the like.

The second port 5430 of the y-adapter 5400 defines a second lumen 5432 with a second diameter $D_2$. As shown in FIG. 7, the second diameter $D_2$ can be configured to be larger than first diameter $D_1$. In other embodiments, the second diameter $D_2$ can be similar or smaller than the first diameter $D_1$. More particularly, the diameter $D_2$ of the second port 5430 is large enough to accept up to, for example, an 18-gauge catheter. The y-adapter 5400 can be of any suitable material and/or be of similar material to that of a conventional y-adapter.

The first lumen 5422 defined by the first port 5420 and the second lumen 5432 defined by the second port 5430 converge to a common lumen 5401 before the distal end 5410 of the y-adapter 5400, as shown in FIG. 7. The second port 5430 is configured such that the second lumen 5432 is substantially coaxial with the common lumen 5401. Furthermore, the common lumen 5401 can have a diameter substantially similar to the diameter $D_2$ of the second port 5430.

The second port 5430 is fluidically coupled to a locking mechanism 5431 configured to couple the y-adapter to the introducer 5100. The locking mechanism 5431 can be a Luer lock or the like. In some embodiments, the y-adapter 5400 is in a sealed configuration until coupled to the locking mechanism 5131 at the distal end 5130 of the introducer 5100. Once the locking mechanism 5431 is coupled to the introducer 5100, the seal can be opened to allow access for the catheter 5200 to advance to a second configuration, shown in FIG. 8 (note the introducer 5100 is not shown coupled to the y-adapter in FIG. 8).

In some embodiments, the distal end 5410 of the y-adapter 5400 is coupled to a peripheral intravenous line 5440 such as, for example, a conventional peripheral intravenous line. In some embodiments, the y-adapter 5400 is monolithically formed with the peripheral intravenous line 5440. In some embodiments, the distal end 5410 of the y-adapter 5400 can be coupled to a peripheral intravenous line using any suitable locking mechanism. Similarly, the second port 5420 of the locking mechanism 5431 configured to couple the y-adapter 5400 to the introducer 5100 can monolithically formed with the introducer 5100. Said another way, in some embodiments, a separate introducer is not required, but rather a portion of the y-adapter can serve as the introducer.

Figure 8:
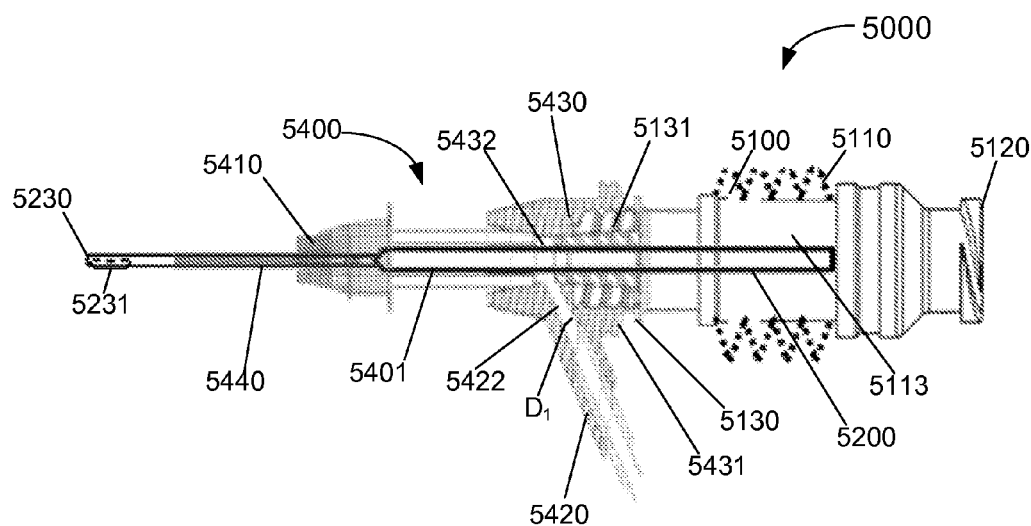
Figure 9:
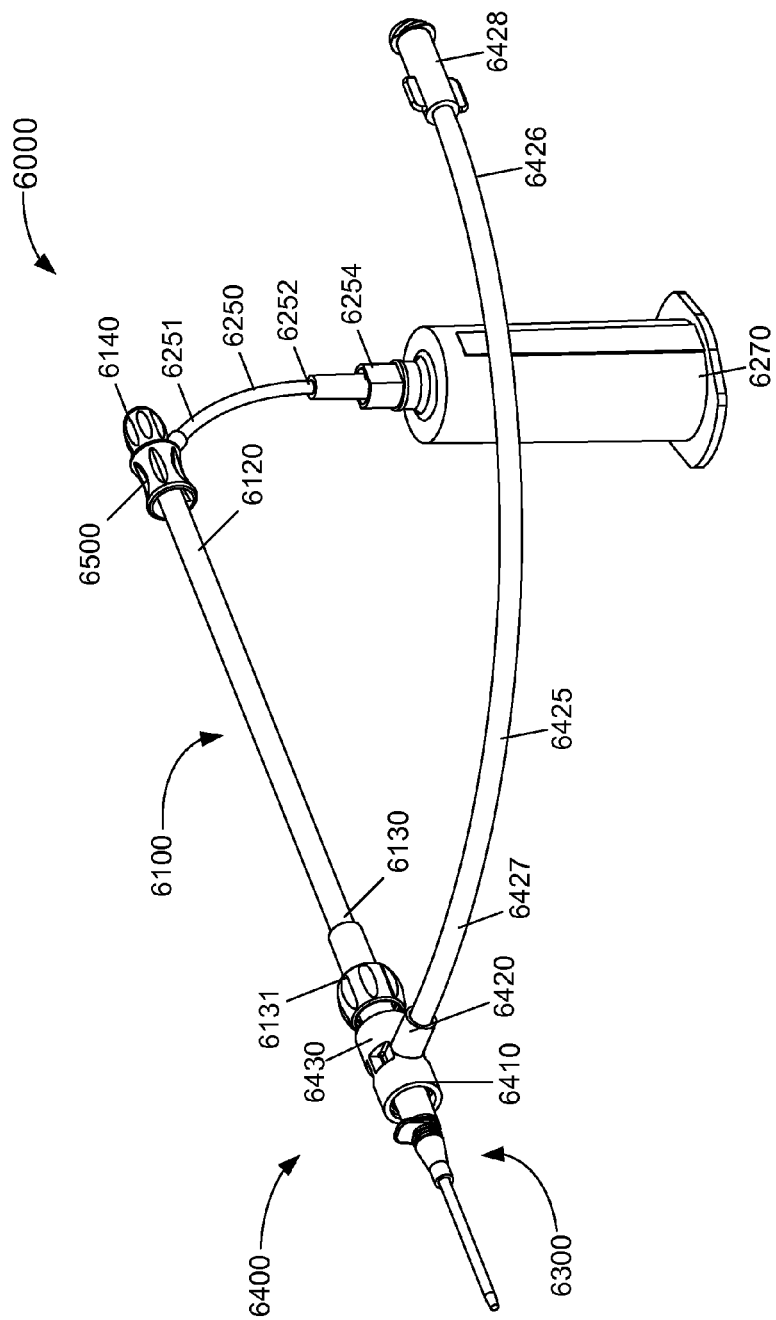
FIG. 9 is a perspective view of an apparatus in a first configuration, according to an embodiment.

When in the second configuration as shown in FIG. 8, the distal end 5230 of the catheter 5200 is advanced substantially past the peripheral intravenous line 5440. The distal end 5230 of the catheter 5200 includes a set of openings 5231 such that when in the second configuration (i.e., when the distal end 5230 of the catheter 5200 is in the vein and outside the intravenous line) the openings 5231 act to transport a bodily fluid (i.e., blood) to a volume outside the catheter 5200. The set of openings 5231 can be of any arrangement on the circumference of the catheter 5200 and can include the end of the catheter 5200. Similarly stated, the catheter 5200 having the distal end 5230 can be substantially open at the tip surface. Each opening 5231 can be of any suitable shape or size and are not necessarily similar to any other opening included in the set of openings. The catheter 5200, in the second configuration and having transported the desired bodily fluid, can be placed in a third configuration (e.g., substantially similar to the first configuration shown in FIG. 7), thereby isolating the used distal end 5230.

While the introducer 5100 (FIGS. 7 and 8) is described as being configured to be substantially compressed to advance the catheter 5200, in other embodiments, an apparatus can include an actuator configured to move the catheter relative to the introducer. For example, FIGS. 9-14 illustrate an apparatus 6000 used for phlebotomy through a peripheral intravenous line. The apparatus 6000 includes an introducer 6100, a cannula 6200, and an adapter 6400. The apparatus 6000 can be any suitable shape, size, or configuration and is configured to be coupled to, for example, a peripheral intravenous line (PIV) 6300.

The introducer 6100 includes a proximal end 6120 and a distal end 6130. As shown in FIGS. 9-14, the introducer 6100 is a substantially cylindrical tube configured to receive the cannula 6200. Similarly stated, the introducer 6100 includes a wall or set of walls that define a lumen 6113 (FIG. 11) configured to selectively receive the cannula 6200. The introducer 6100 and cannula 6200 can be formed from any suitable material having any given durometer. In some embodiments, the cannula 6200 can have a durometer between 20 Shore A and 50 Shore D. In other embodiments, the cannula 6200 can have a Shore durometer of approximately 20 Shore A to 95

Shore D. In still other embodiments, the cannula 6200 can have a Shore durometer of approximately 70 Shore D to 85 Shore D.

The proximal end 6120 of the introducer 6100 is configured to be coupled to an end cap 6140. In this manner, the end cap 6140 can be configured to substantially close off and/or seal the proximal end 6120 of the introducer 6100. In some embodiments, the end cap 6140 is configured to form a substantially fluid-tight seal with the introducer 6100. Similarly stated, in some embodiments, the end cap 6140 and the proximal end 6120 of the introducer 6100 define a substantially hermetic seal. In some embodiments, the end cap 6140 can be grasped by a user as the cannula 6200 is advanced.

The distal end 6130 of the introducer 6100 is coupled to a lock mechanism 6131. The lock mechanism 6131 is configured to physically and fluidically couple a portion of the apparatus 6000 to the existing PIV 6300. In some embodiments, the lock mechanism 6131 can be configured to be directly coupled to the existing PIV 6300. In other embodiments, the lock mechanism 6131 can be coupled to the adapter 6400 and/or any other suitable intervening structure, such as, for example, a known valve or cap.

The distal end 6130 of the introducer 6100 can be coupled to the lock mechanism 6131 in any suitable manner. For example, in some embodiments, the distal end 6130 can be disposed within a portion of the lock mechanism 6131 such that an outer surface of the introducer 6100 defines a friction fit with the inner surface of the portion of the lock mechanism 6131. In other embodiments, the distal end 6130 of the introducer 6100 can be coupled to the lock mechanism 6131 via an adhesive. In still other embodiments, the lock mechanism 6131 can be monolithically formed with the distal end 6130 of the introducer 6100. For example, in some embodiments, the lock mechanism 6131 can be formed from a similar material as the introducer 6100. In other embodiments, the introducer 6100 can be formed from a first material and the lock mechanism 6131 can be formed from a second material configured to be over-molded the distal end 6130 during a manufacturing process.

Figure 11:
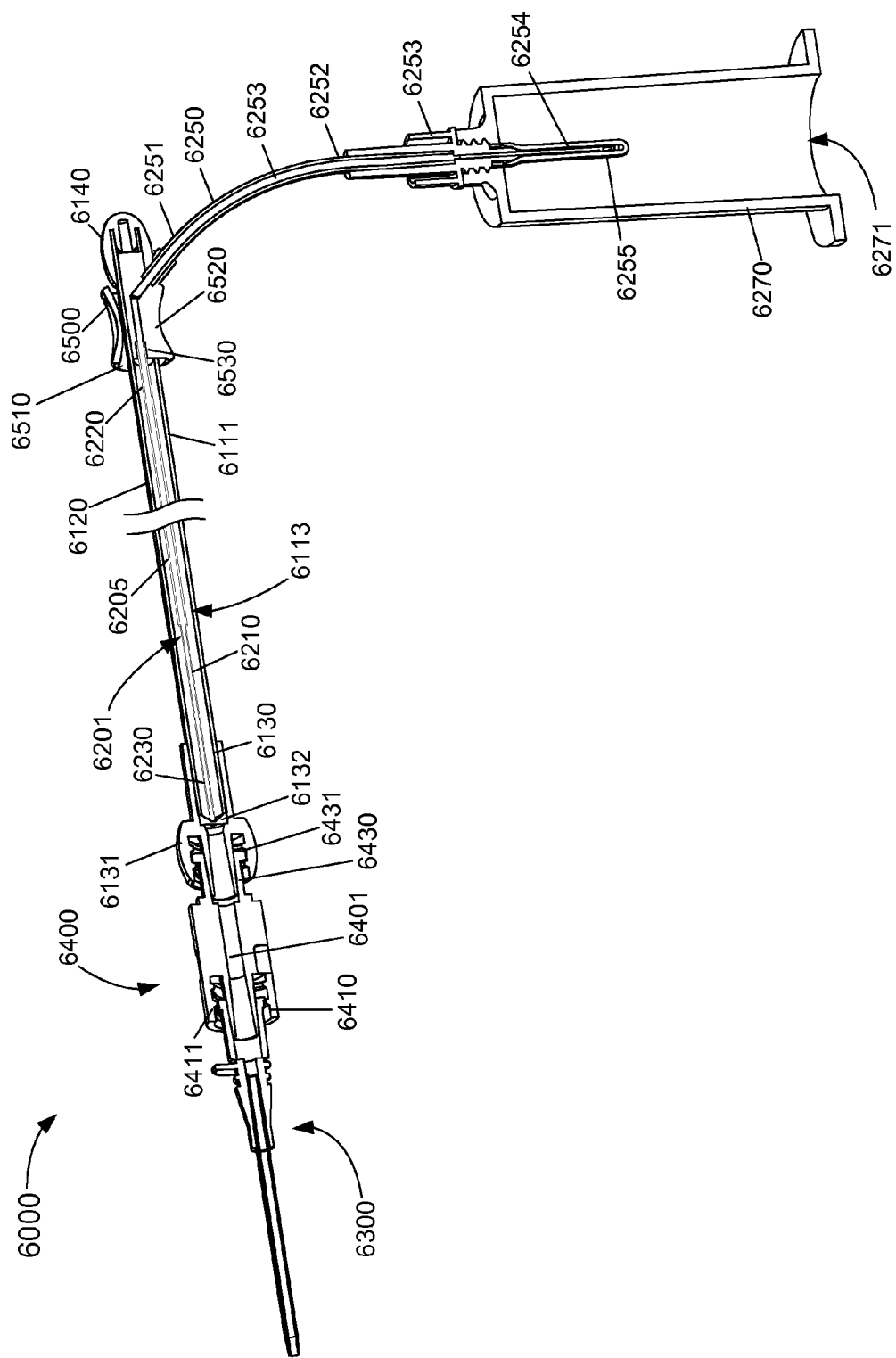
FIG. 11 is a cross-sectional perspective view of the apparatus illustrated in FIG. 9.

As seen in FIG. 11, the lock mechanism 6131, includes a seal member 6132 configured to define a substantially fluid tight seal when the cannula 6200 is in the first configuration. Furthermore, in use, the seal member 6132 can be configured to receive a portion of the cannula 6200 to allow the cannula 6200 to advance, in the distal direction, beyond the seal member 6132. In this manner, the seal member 6132 can form a substantially fluid tight seal around the cannula 6200 such that the seal member 6132 substantially prevents a backflow into the introducer 6100. The seal member 6132 can be any suitable configuration such as, for example, an o-ring, a one way valve, a diaphragm, a check valve, or any other suitable seal member. While shown and described as being included in the locking mechanism 6131, in some embodiments, a seal member can be included in the locking mechanism 6131 and/or the adapter 6400. For example, in some embodiments, the locking mechanism 6131 can be coupled to the adapter 6400 such that the seal member included in the adapter 6400 and/or the locking mechanism 6131 prevents a flow of bodily fluid in the proximal direction prior to advancing the cannula 6200, as further described herein.

Figure 10:
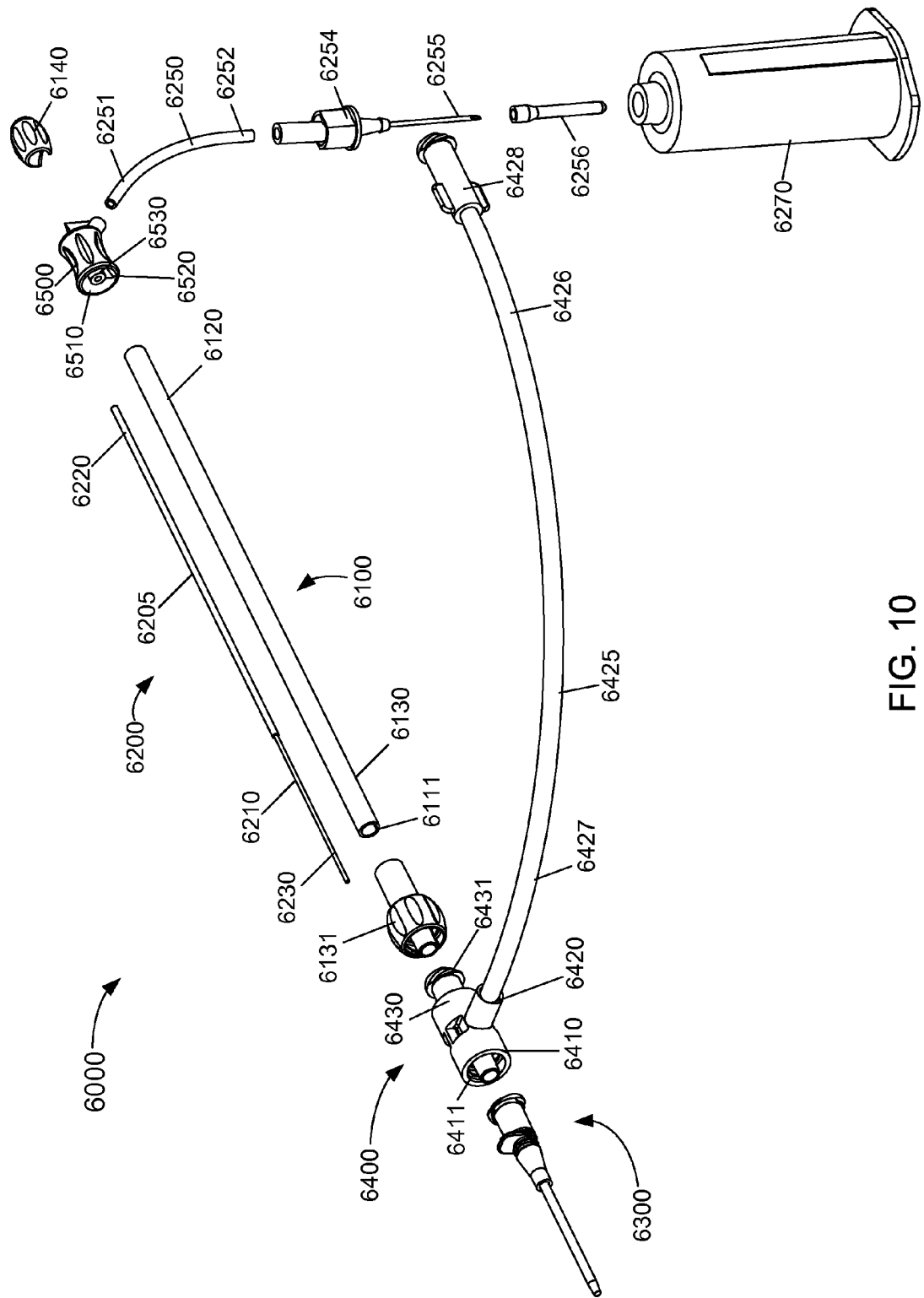
FIG. 10 is an exploded view of the apparatus illustrated in FIG. 9.

As seen in FIGS. 10 and 11, the introducer 6100 further defines an actuator track 6111. The actuator track 6111 can be a slit or opening defined by the wall of the introducer 6100 and is configured to receive a portion of the actuator 6500. The actuator track 6111 can be configured to extend substantially along the length of the introducer 6100. In some embodiments, the actuator track 6111 is configured to continuously extend through the distal end 6130 and the proximal end 6120 of the introducer 6100. The actuator track 6111 can be any suitable configuration and can engage the portion of the actuator 6500 in any suitable manner. For example, in some embodiments, the walls of the introducer 6100 defining the actuator track 6111 can form a friction fit with the portion of the actuator 6500, as described in further detail herein.

The cannula 6200 defines a lumen 6201 (FIG. 11) and is configured to be movably disposed within the introducer 6100. As described above with reference to FIG. 5, the cannula 6200 can be configured to include a first portion 6205 having a first diameter and a second portion 6210 having a second diameter, smaller than the first. More specifically, the first portion 6205 is disposed at a proximal end 6220 of the cannula 6200 and the second portion 6210 is disposed at a distal end 6230 of the cannula 6200. In this manner, for example, the diameter of the cannula 6200 is reduced at the distal end 6230 of the catheter 6200 to facilitate the insertion of the catheter 6200 into the peripheral intravenous line, as described in further detail herein.

As described above with reference to FIG. 6A, the distal end 6230 of the cannula 6200 can be configured to include any suitable number of openings (not shown in FIGS. 9-14. For example, in some embodiments, the distal end 6230 of the cannula 6200 can include a substantially open end surface configured to place the lumen 6201 in fluid communication with, for example, a vein. In some embodiments, the end surface can be substantially flat (e.g., perpendicular to a longitudinal axis of the cannula 6200. In other embodiments, the end surface can be any suitable configuration such as, for example, substantially bullet-shaped, conical, bulbous, or the like. In still other embodiments, the end surface can be substantially angled with respect to the longitudinal axis of the cannula 6200 (e.g., similar to the tip of a needle). Furthermore, in some embodiments, the distal end 6230 can be configured to include the open end surface and an opening disposed on the side of the cannula 6200. In this manner, the side opening (not shown in FIGS. 9-14) can be configured to transfer a portion of a bodily fluid even if the opening disposed at the end surface is obstructed (e.g., by a clot or the like).

The actuator 6500 is coupled to the proximal end 6220 of the cannula 6200 and is configured to move the cannula 6200, relative to the introducer 6100, between a first configuration and a second configuration. More specifically, the actuator 6500 defines a substantially annular shape defining a cavity 6510 configured to receive the proximal end 6120 of the introducer 6100 and the proximal end 6220 of the cannula 6200. Similarly stated, the actuator 6500 is disposed about the introducer 6100 and the cannula 6200. Furthermore, the actuator 6500 is configured such that a guide member 6520 and a coupler 6530 extend from an inner surface of the actuator 6500.

The guide member 6520 can be any suitable shape, size, or configuration. For example, as shown in FIG. 10, the guide member 6520 is a relatively thin extension. In this manner, the guide member 6520 is disposed within the actuator track 6111 when the actuator 6500 is disposed about the introducer 6100. In some embodiments, the walls of the introducer 6100 defining the actuator track 6111 define a friction fit with a portion of the guide member 6520. The arrangement of the guide member 6520 within the actuator track 6111 can be such that the actuator 6500 is substantially maintained in a given location, relative to the introducer 6100, until a force is applied to the actuator 6500 to move the actuator 6500 towards the second configuration. Similarly stated, the actuator 6500 engages the introducer 6100 such that the actuator

6500 substantially does not move without a user's intervention (e.g., applying a force to the actuator 6500). In other embodiments, the actuator 6500 need not include a guide member 6520. In such embodiments, the actuator 6500 can be configured to define a friction fit with the introducer 6100 when the actuator 6500 is disposed about the introducer 6100 (e.g., an inner surface of the wall or walls defining the annular shape of the actuator 6500 engage an outer surface of the introducer 6100 to define the friction fit).

Figures 13, 13A:
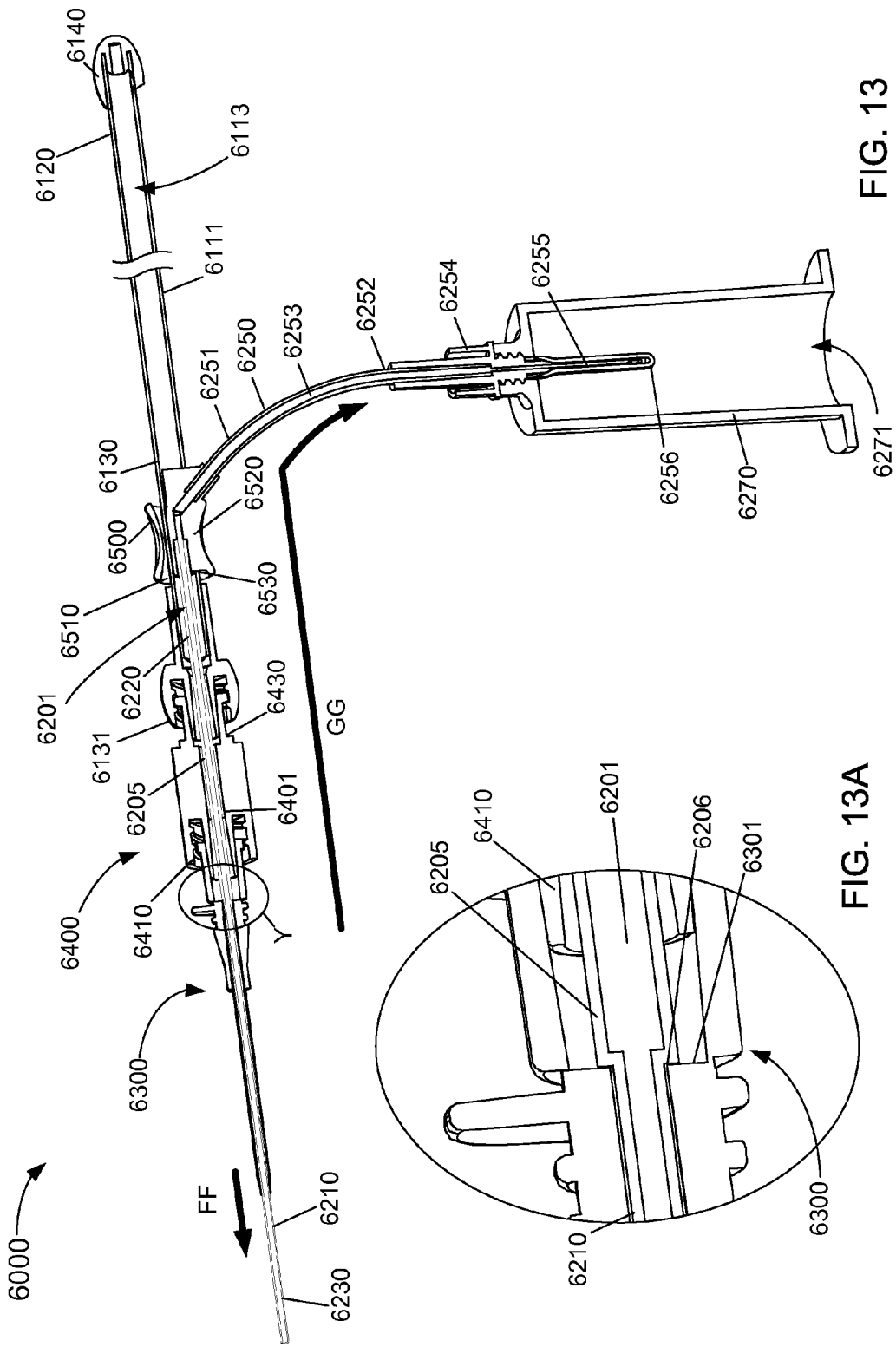
FIG. 13 is a cross-sectional perspective view of the apparatus illustrated in FIG. 9, in the second configuration.
FIG. 13A is an enlarged view of a portion of the apparatus of FIG. 13, indicated by the region Y.

The coupler 6530 is disposed on a top surface of the guide member 6520 (e.g., the guide member 6520 is disposed between the coupler 6530 and the inner surface of the actuator 6500). As shown in FIGS. 11 and 13, the coupler 6530 is coupled to the proximal end 6220 of the cannula 6200. In some embodiments, an outer surface of the proximal end 6220 of the cannula 6200 defines a friction fit with the inner surface of the coupler 6530. In other embodiments, the distal end 6220 of the cannula 6200 can be coupled to the coupler 6530 via an adhesive. In this manner, the proximal end 6220 of the cannula 6200 and the coupler 6530 form a substantially fluid tight seal.

A proximal end 6540 of the actuator 6500 is coupled to a secondary cannula 6250 further configured to be coupled to a container shroud 6270. The container shroud 6270 defines a cavity 6271 configured to receive fluid reservoir (e.g., a conventional phlebotomy fluid container such as a Vacutainer®). More specifically, secondary cannula 6250 defines a lumen 6253 and includes a proximal end 6252 configured to be coupled to a lock mechanism 6524. The lock mechanism 6524 can be configured to be coupled to the container shroud 6270. In addition, the lock mechanism 6524 includes a needle 6525 disposed within a sheath 6526 configured to pierce a portion of the fluid reservoir (e.g., as described above with reference to FIG. 3) when the fluid reservoir (not shown) is disposed within the container shroud 6270. Therefore, with the proximal end 6220 of the cannula 6200 coupled to the coupler 6530 and the secondary cannula 6250 coupled to the proximal end 6540 of the adapter 6500, the adapter 6500 is configured to place the cannula 6200 (e.g., the lumen 6201 defined by the cannula 6200) in fluid communication with the secondary cannula 6250 (e.g., the lumen 6253 of the secondary cannula 6250) and the fluid reservoir (not shown).

While described as including the secondary cannula 6250, in some embodiments, the apparatus 6000 need not include the secondary cannula 6250. In such embodiments, the cannula 6200 can define a continuous fluid path (e.g., lumen 6201) from the distal end 6230, through the connector 6530, and to the container shroud 6270. In other embodiments, the container shroud 6270 can be configured to be physically and fluidically coupled to the actuator 6500.

The adapter 6400 can be any suitable adapter 6400. For example, in some embodiments, an adapter can be a known Y-adapter or T-adapter (e.g., a dual port IV extension set). In other embodiments, an adapter can be similar in form and function to the adapter 5400, described above with reference to FIGS. 7 and 8. As shown in FIG. 10, the adapter 6400 is a T-style adapter and includes a distal end 6410, a first port 6420, and a second port 6430. The distal end 6410 defines a port and includes a lock mechanism 6411 configured to be coupled to the peripheral intravenous line 6300. In this manner, the lock mechanism 6411 can be any suitable known lock mechanism such that the distal end 6410 of the adapter 6400 can engage a known PIV 6300.

The first port 6420 can be coupled to a distal end 6427 of an inlet catheter 6425. In some embodiments, the distal end 6427 of the inlet catheter 6425 forms a friction fit with an inner surface of the first port 6420. In some embodiments, the distal end 6427 of the inlet catheter 6425 can include a fitting configured to engage the first port 6420 (e.g., a threaded fitting). In other embodiments, the inlet catheter 6425 can be monolithically formed with the first port 6420 of the adapter 6400. The inlet catheter 6425 further includes a proximal end 6426 configured to couple to a lock mechanism 6428. In this manner, the inlet catheter 6425 can be engaged by a user (e.g., a physician, nurse, or the like) to administer a fluid (e.g., a medicine or the like) to the peripheral intravenous line and thus, the vein of a patient. In some embodiments, the inlet catheter 6425 is substantially similar in form and function as known inlet catheters. Therefore, with the adapter 6400 coupled to the PIV 6300 and the PIV 6300 disposed within a patient, a user can administer a given fluid to the patient via the inlet catheter 6425 without requiring further training in the functioning of the adapter 6400.

Figure 12:
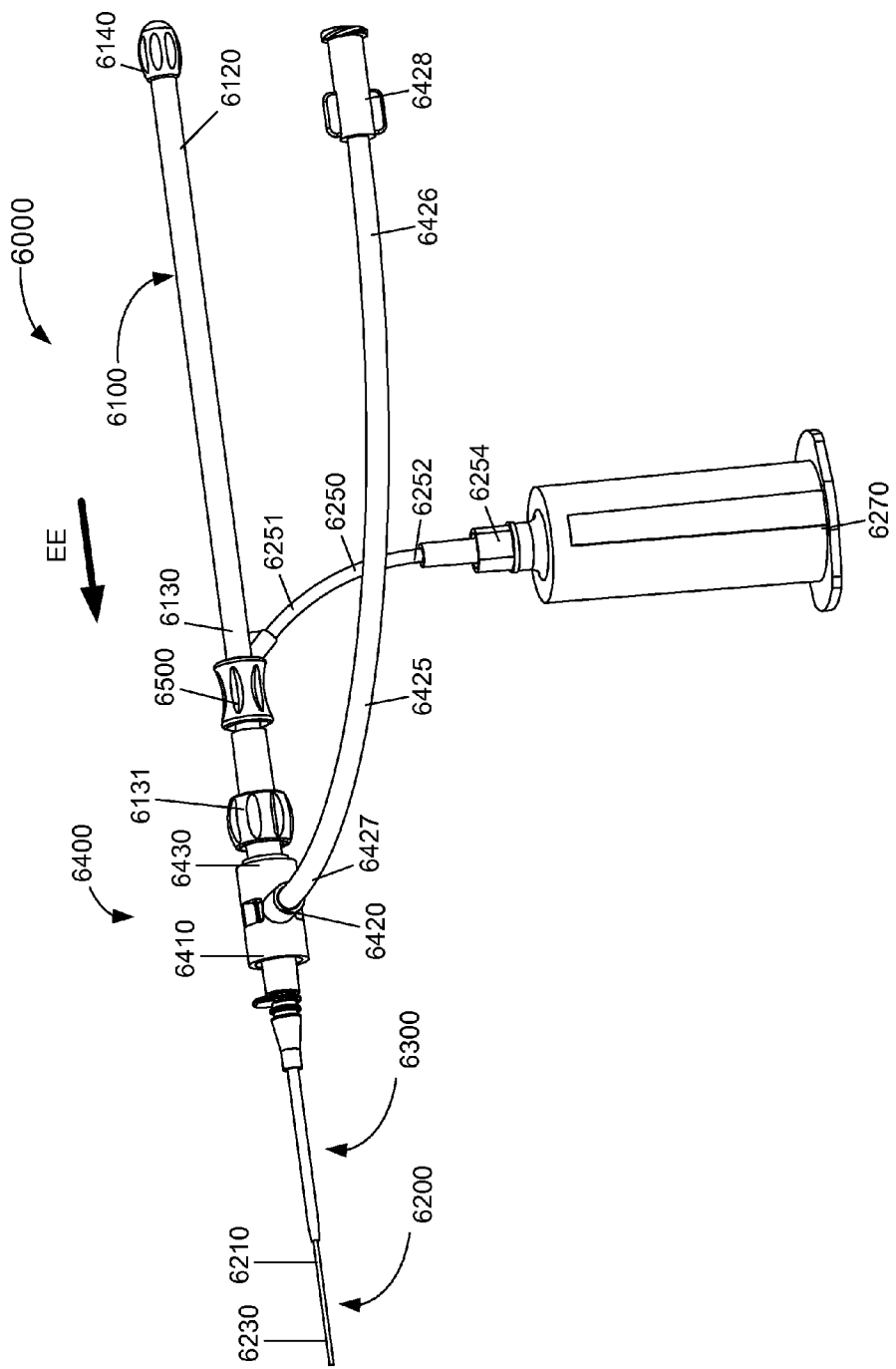
FIG. 12 is a perspective view of the apparatus illustrated in FIG. 9, in a second configuration.

In use, a user (e.g., a phlebotomist) can engage the actuator 6500 of the blood draw apparatus 6000 to move the actuator 6500 in the distal direction, as indicated by the arrow EE in FIG. 12. In this manner, the actuator 6500 moves in the distal direction relative to the introducer 6100 to place the apparatus in the second configuration. As described above, the user can apply a sufficient amount of force to the actuator 6500 such that the friction between the walls of the introducer 6100 and the guide member 6520 of the actuator 6500 is overcome. With the cannula 6200 coupled to the coupler 6530 of the actuator 6500, the cannula 6200 is moved in the distal direction concurrently with the actuator 6500 toward the second configuration.

As indicated by the arrow FF in FIG. 13, the cannula 6200 is advanced through the seal member 6132 included in the lock mechanism 6131, through a lumen 6401 defined by the adapter 6400 and through the PIV 6300 such that the distal end 6230 of the cannula 6200 extends beyond the PIV 6300. In this manner, the distal end 6230 of the cannula 6200 is substantially disposed within the vein of the patient such that the lumen 6201, defined by the cannula 6200, is in fluid communication with the vein. As shown in FIG. 13A, the cannula 6200 can be advanced through the PIV 6300 such that a distal surface 6206 of the first portion 6205 of the cannula 6200 is placed in contact with a proximal surface 6301 of a portion of the PIV 6300. Thus, the distal surface 6206 of the cannula 6200 engages the proximal surface 6301 of the PIV 6300 to prevent the cannula 6200 from being advanced beyond the second configuration. Similarly stated, the distal surface 6206 is configured to contact the proximal surface 6301 of the portion of the PIV 6300 to limit the travel of the cannula 6200. While the first portion 6205 and the second portion 6210 of the cannula 6200 shown in FIG. 13A include a substantially similar inner diameter, in other embodiments, the first portion 6205 can have a substantially larger inner diameter than the second portion 6210. In some embodiments, an inner wall or a set of inner walls that define the lumen 6201 can include a tapered transition between the first portion 6205 and the second portion 6210. In other embodiments, the inner wall or walls need not include a tapered portion.

While not shown in FIG. 13, a fluid container (e.g., a Vacutainer®) can be disposed within the cavity 6271 defined by the container shroud 6270 such that the sheath 6256 is withdrawn from the needle 6255 and the needle 6255 pierces the fluid container, thereby placing the fluid container in fluid communication with the vein of the patient. In other embodiments, the fluid container can be monolithically formed with the container shroud 6270 and/or with the introducer and the movement of the actuator 6500 can urge the needle 6255 to pierce the fluid container. In some embodiments, the fluid container is configured to define a negative pressure (e.g., a Vacutainer®). In such embodiments, when the needle 6255 pierces the fluid container, the negative pressure within the fluid container introduces a suction force within the lumen 6253 of the secondary cannula 6250 and the lumen 6201 of the cannula 6200. The suction force is such that a bodily fluid (e.g., blood) is drawn through the lumen 6201 of the cannula 6200 and the lumen 6253 of the secondary cannula 6250 and into the fluid container, as indicated by the arrow GG in FIG. 13. In this manner, a phlebotomist can collect (e.g., draw) a given amount of blood through an existing peripheral intravenous line without the need for additional needle sticks.

Figure 14:
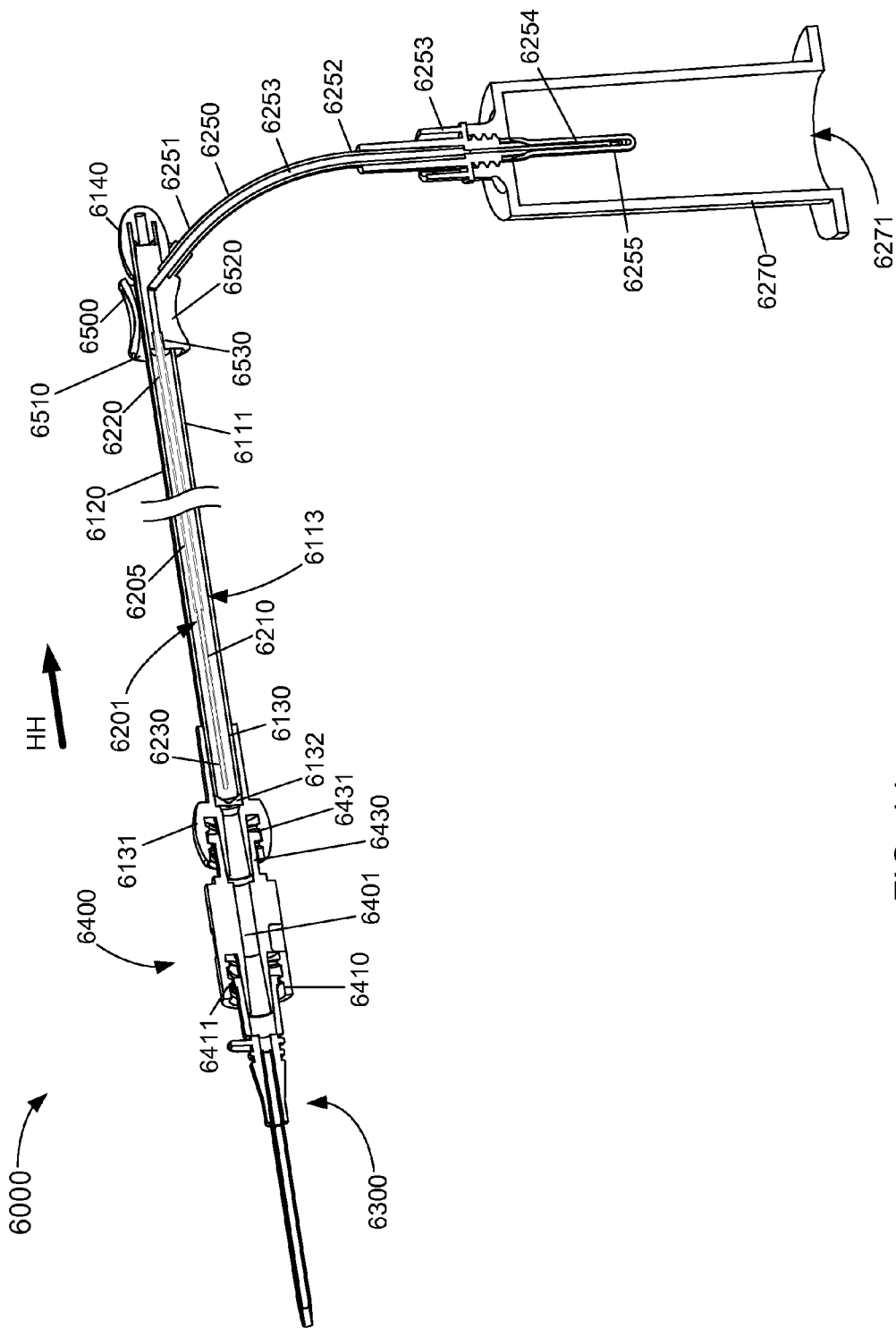
FIG. 14 is a cross-sectional perspective view of the apparatus illustrated in FIG. 9, in a third configuration.

With the desired amount of bodily fluid collected, the user (e.g., phlebotomist) can move the actuator 6500 in the proximal direction, thereby placing the apparatus 6000 in a third (used) configuration, as indicated by the arrow HH in FIG. 14. In the third configuration, the cannula 6200 is substantially fluidically isolated from a volume outside the introduce 6100. Therefore, the introducer 6100 (e.g., the lock mechanism 6131) can be decoupled from the second port 6430 of the adapter 6400 and safely discarded.

Figure 17:
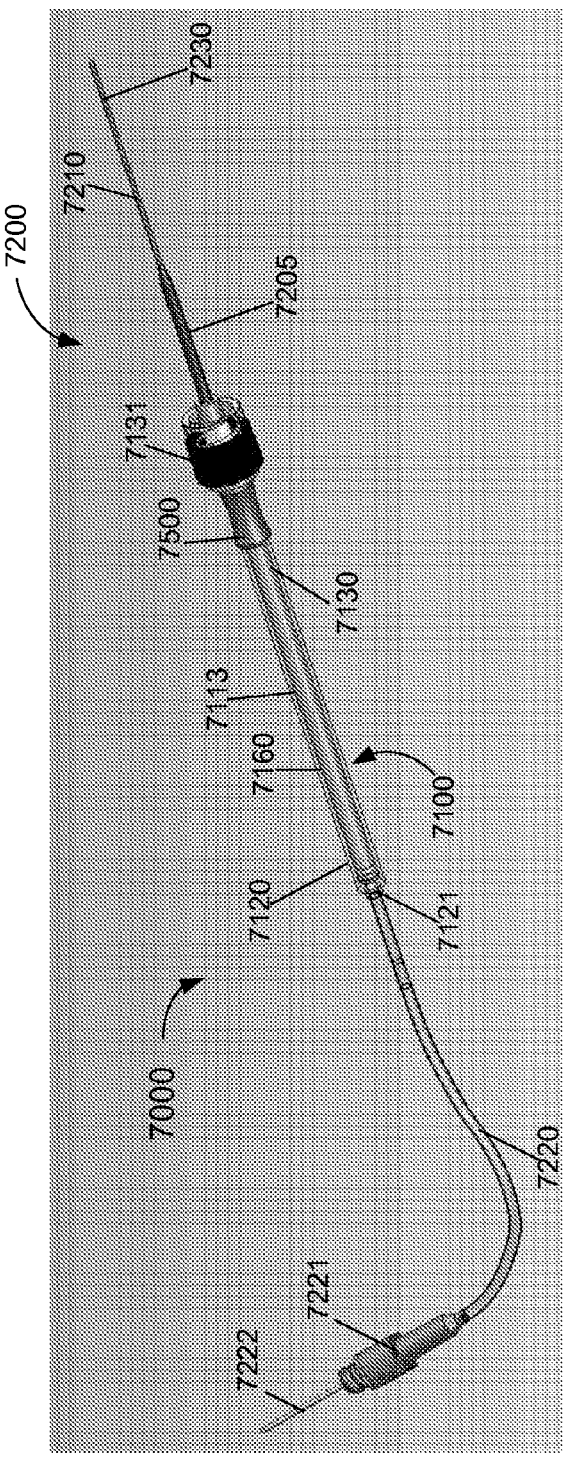
FIG. 17 is a perspective view of the apparatus illustrated in FIG. 15, in the second configuration.

While the apparatus 6000 (shown and described with respect to FIGS. 9-14) includes a single piece introducer 6100, in some embodiments, an apparatus can include a multi-piece introducer configured for telescopic motion. For example, FIGS. 15-22 illustrate an apparatus 7000 according to an embodiment. As shown in FIGS. 15-17, the apparatus 7000 includes an introducer 7100 and a cannula 7200 and is configured to be moved between a first configuration (FIG. 15) and a second configuration (FIGS. 16 and 17), as described in further detail herein.

The introducer 7100 includes a first member 7150 defining a first lumen 7155 and a second member 7160 defining a second lumen 7165. In some embodiments, the first member 7150 is a substantially cylindrical tube having a first diameter and the second member 7160 is a substantially cylindrical tube having a second diameter, larger than the first diameter. In this manner, the lumen 7165 defined by the second member 7160 is configured to receive at least a portion of the first member 7155. More specifically, the first member 7150 is movably disposed within the second member 7165 such that the introducer 7100 can be moved in a telescopic motion. Similarly stated, the second member 7160 is configured to move between a first position and a second position, relative to the first member 7150. Furthermore, the second member 7160 includes an actuator portion 7500 configured to be engaged by a user (e.g., a phlebotomist) to move the second member 7160 relative to the first member 7150.

The introducer 7100 includes a proximal end 7120 and a distal end 7130. The proximal end 7120 includes a port 7121. The port 7121 can be any suitable port. For example, in some embodiments, the port 7121 is substantially similar to the port 1121, described above with reference to FIGS. 1 and 2. In this manner, the port 7121 is configured to receive a portion of the catheter 7200, as described in further detail herein. The distal end 7130 can be coupled to a lock mechanism 7131. The lock mechanism 7131 can be any suitable mechanism such as, for example, a Luer lock. In some embodiments, the lock mechanism 7131 can be substantially similar to the lock mechanism 6131 described above with reference to FIGS. 9-14. Therefore, the lock mechanism 7131 is not described in further detail herein.

The introducer 7100 is configured to receive at least a portion of the cannula 7200. More specifically, the cannula 7200 includes a proximal end 7220 and a distal end 7230 and is at least partially disposed within the introducer 7100 such that the proximal end 7220 of the cannula 7200 extends through the port 7121 of the introducer 7100. In this manner, the cannula 7200 is configured to move relative to at least a portion of the introducer 7100 between a first configuration and a second configuration, as further described herein.

The proximal end 7220 of the cannula 7200 is coupled to a lock mechanism 7221. The lock mechanism 7221 can be any suitable lock mechanism, such as, for example, a Luer lock. Furthermore, the lock mechanism 7221 is coupled to a needle 7222 such that when the proximal end 7220 of the cannula 7200 is coupled to the lock mechanism 7221, a lumen (not shown in FIGS. 15-22) defined by the cannula 7200 is placed in fluid communication with a lumen (not shown in FIGS. 15-22) defined by the needle 7222. The distal end 7230 of the cannula 7200 includes a first portion 7205, having a first diameter, and a second portion 7210, having a second diameter, smaller than the first diameter. As shown in FIG. 17, the cannula 7200 is configured to include a taper between the first portion 7205 and the second portion 7210. The taper can be any suitable configuration and can be substantially similar to the taper portion 4203 described above with reference to FIG. 5.

Figure 18:
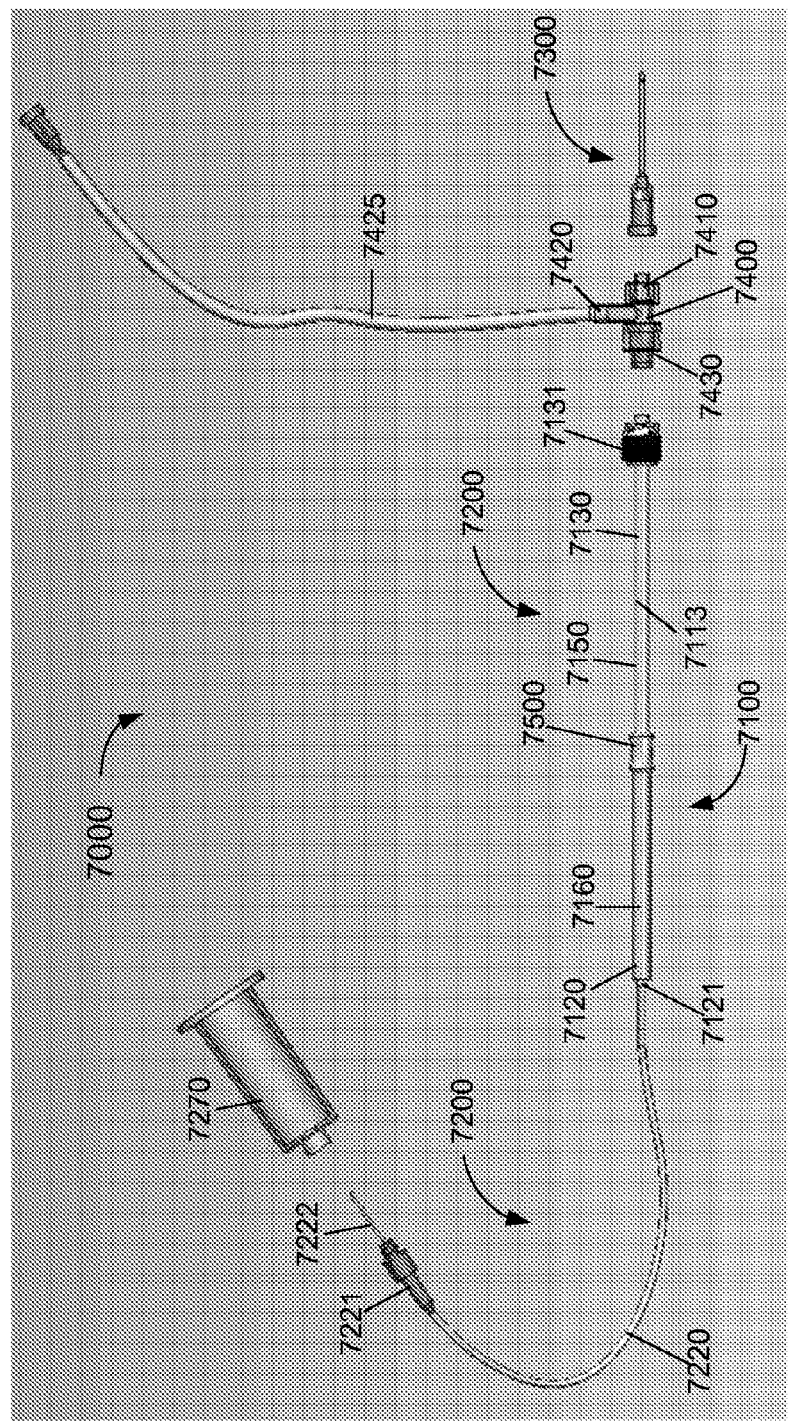
FIG. 18 is an exploded side view of the apparatus of FIG. 15 and an adapter, according to an embodiment.

As shown in the exploded view of FIG. 18, the lock mechanism 7131 is configured to be coupled to an adapter 7400. The adapter includes a distal end 7410, a first port 7420, and a second port 7430. The adapter 7400 can be any suitable adapter described herein. For example, in some embodiments, the adapter can be substantially similar to the adapter 6400 described above with reference to FIGS. 9-14. In other embodiments, the adapter 7400 can be any known adapter, such as, for example, a Y-adapter or a T-adapter. In this manner, the first port 7420 of the adapter 7400 is configured to be coupled to an inlet catheter 7425. The inlet catheter 7425 can be any suitable configuration. In some embodiments, the inlet catheter 7425 is substantially similar in form and function to the inlet catheter 6425 described above with reference to FIGS. 9-14. Therefore, the inlet catheter 7425 is not described in detail herein.

The second port 7430 is configured to be coupled to the lock mechanism 7131. In this manner, the second port 7430 and the lock mechanism 7131 can be configured to form a substantially fluid tight seal. For example, in some embodiments, the second port 7430 can include a threaded coupling configured to engage a threaded coupling of the lock mechanism 7131, thereby defining the substantially fluid tight seal. Furthermore, the lock mechanism 7131 can include a seal member (not shown in FIGS. 15-22) configured to selectively fluidically isolate a lumen 7113 defined by the introducer 7100 from a lumen (not shown) defined by the adapter. For example, in some embodiments, the seal member can be substantially similar in form and function to the seal member 6132 described above with reference to FIG. 11. The distal end 7410 of the adapter 7400 is configured to be coupled to a peripheral intravenous line (PIV) 7300. In some embodiments, the PIV 7300 is a known PIV. In this manner, the distal end 7410 of the adapter 7400 can include any suitable feature configured to physically and fluidically couple the adapter 7400 to the PIV 7300.

Figure 19:
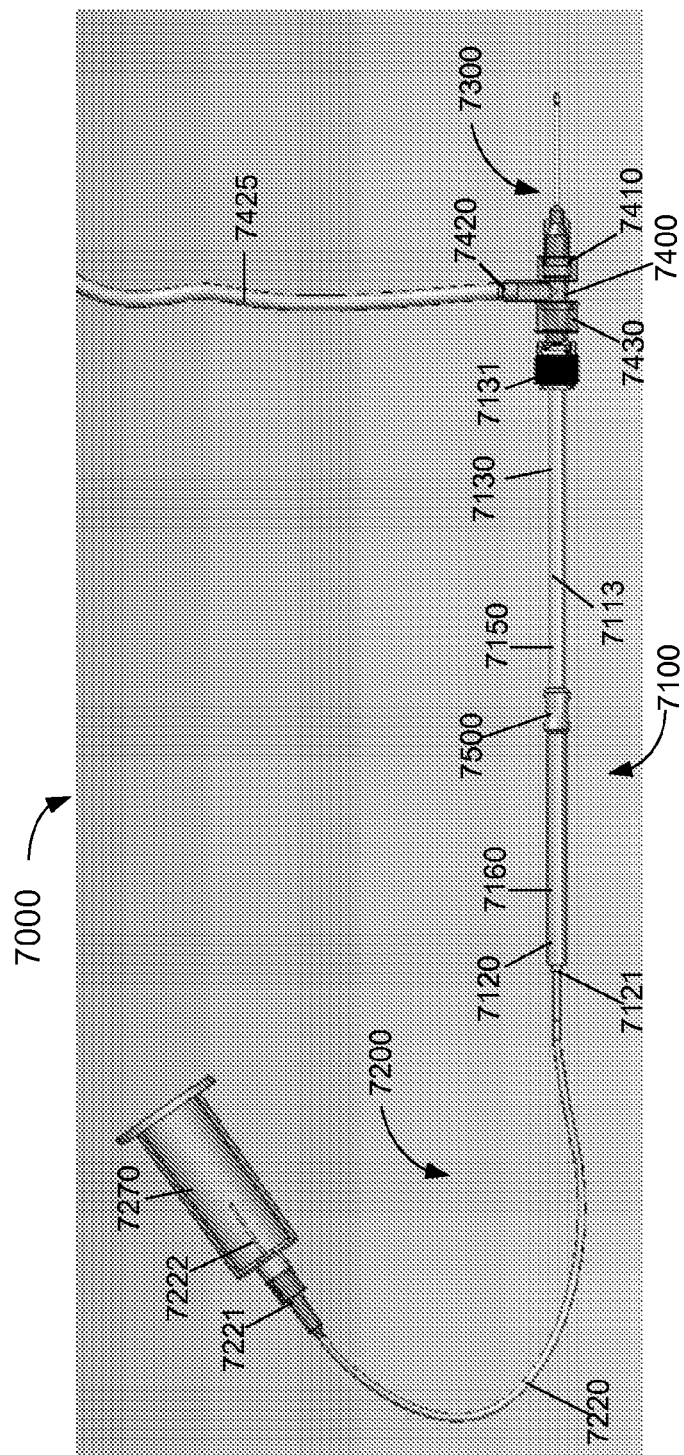
FIG. 19 is a side view of the apparatus and adapter illustrated in FIG. 18, in a first configuration.
Figure 20:
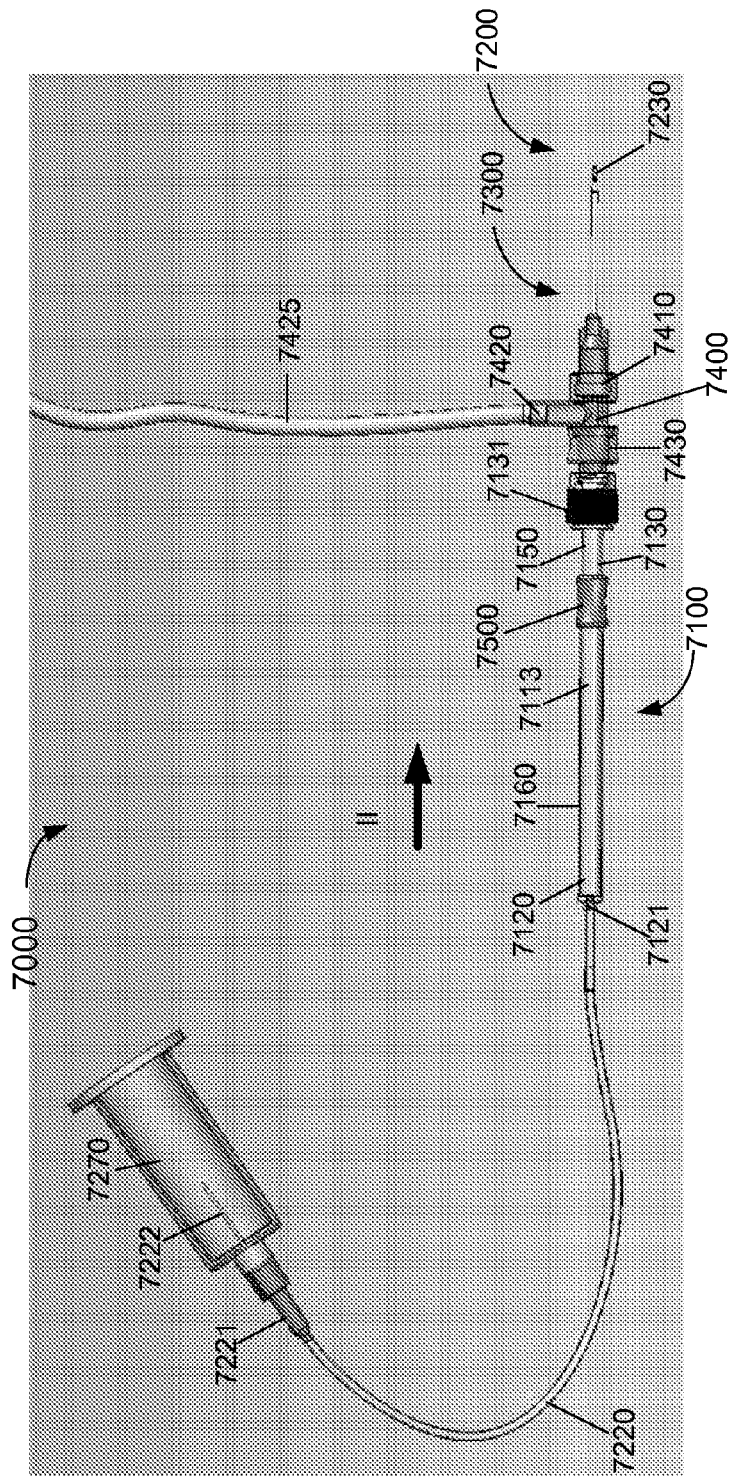
FIG. 20 is a side view of the apparatus and the adapter illustrated in FIG. 18, in a second configuration.
Figure 21:
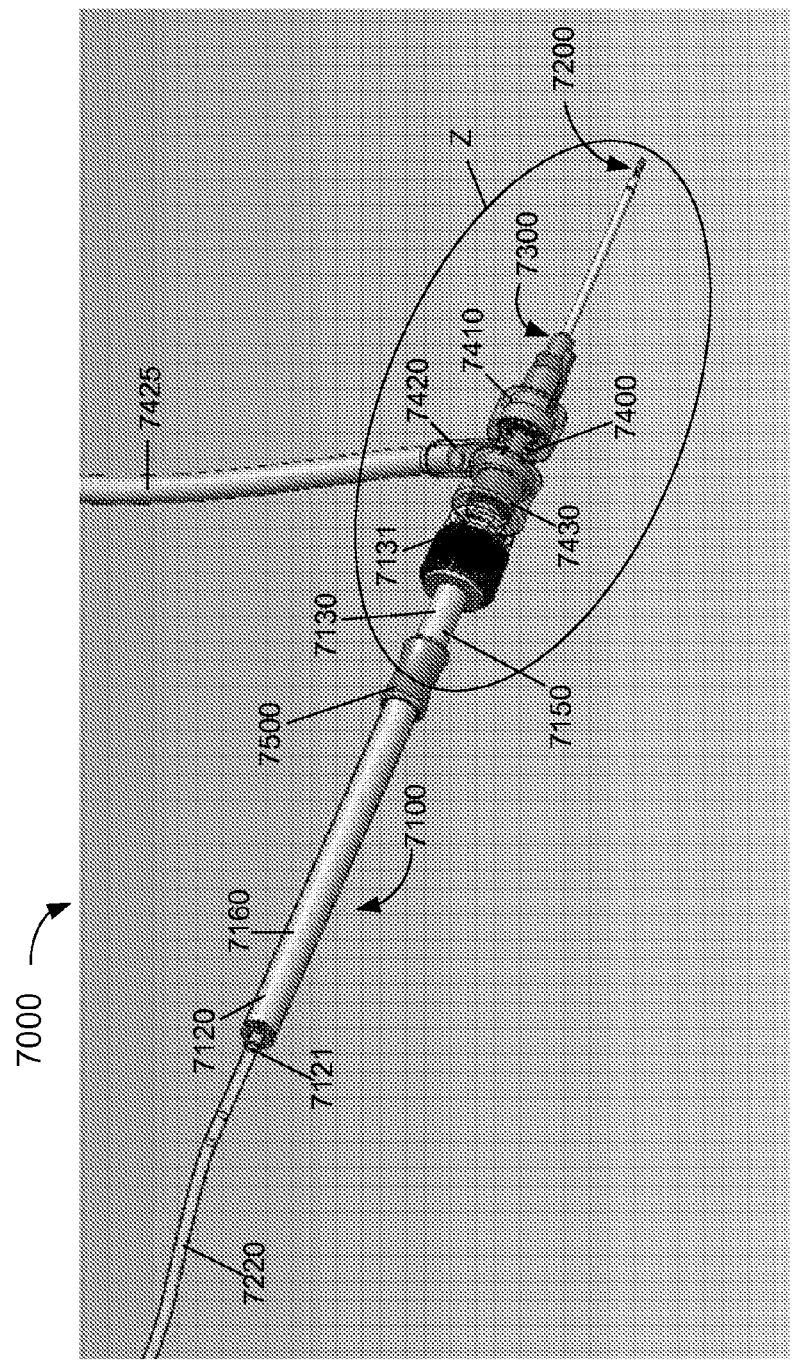
FIG. 21 is a perspective view of the apparatus illustrated in FIG. 18, in the second configuration.
Figure 22:
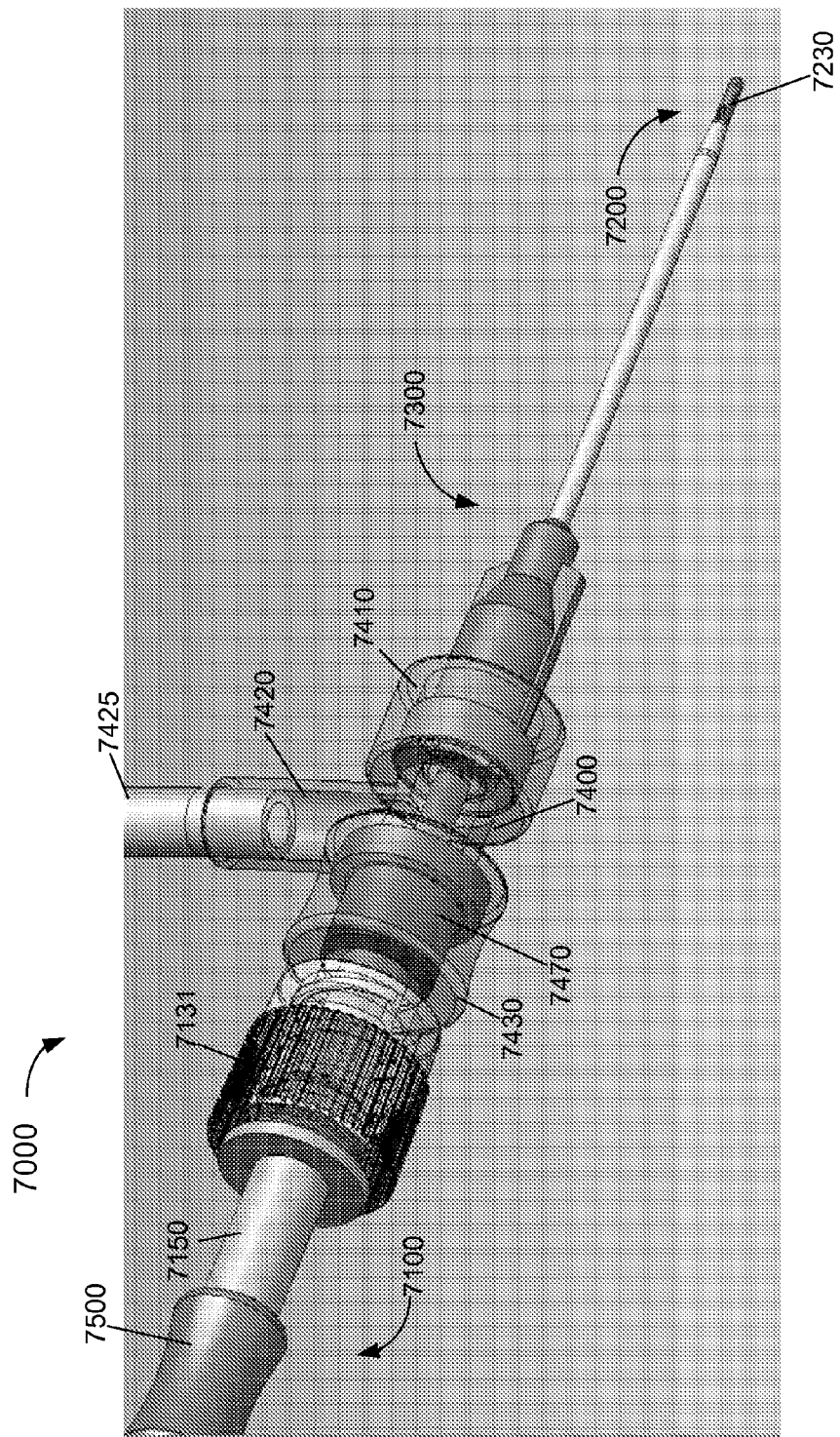
FIG. 22 is an enlarged view of a portion of the apparatus of FIG. 18, indicated by the region Z in FIG. 21.

As shown in FIG. 19, the apparatus 7000 can be in the first configuration such that the second member 7260 of the introducer 7100 is disposed in a proximal position relative to the first member 7150 of the introducer 7100. In use, a user (e.g., a phlebotomist) can engage the actuator 7500 included in the second member 7160 of the introducer 7100 and move the second member 7160 in the distal direction, as indicated by the arrow II in FIG. 20. In this manner, the introducer 7100 moves in a telescopic motion such that the second member 7160 moves relative to the first member 7150. Similarly stated, an overall length of the introducer 7100 is reduced when the second member 7160 moves relative the first member 7150. Furthermore, the distal movement of the second member 7160 is such that the cannula 7200 is moved in the distal direction. In this manner, the distal end 7230 of the cannula 7200 passes through the seal member included in the lock mechanism 7131 (as similarly described above in reference to FIGS. 11 and 13) and through the PIV 7300. As shown in the enlarged view of FIG. 22, the distal end 7230 of the cannula 7200 extends beyond the PIV 7300 to place a lumen (not shown) defined by the cannula 7200 in fluid communication with a portion of a body of a patient (e.g., a vein). Furthermore, in some embodiments, the adapter 7400 can be configured to include a seal member 7470 configured to receive the cannula 6200. In this manner, the seal member 7470 can prevent a backflow of a bodily fluid into, for example, the introducer 7100.

With the apparatus 7000 in the second configuration (e.g., FIGS. 20-22), the user can dispose a fluid container (e.g., a Vacutainer®, or any other suitable fluid container) within a container shroud 7270 such that the container engages the needle 7222. In this manner, the needle 7222 can pierce a portion of the fluid container (not shown) to place the fluid container in fluid communication with the lumen defined by the cannula 7200. In addition, with the distal end 7230 of the cannula 7200 disposed within, for example, the vein of the patient, the fluid container can be placed in fluid communication with the vein. In some embodiments, such as those where the fluid container is a Vacutainer® or the like, the fluid container can define a negative pressure (e.g., the fluid container is an evacuated container). In such embodiments, the negative pressure defined by the fluid container can introduce a suction force to the lumen defined by the cannula 7200 such that a bodily fluid (e.g., blood) is drawn through the cannula 7200 and into the fluid container. In this manner, a phlebotomist can collect (e.g., draw) a given amount of blood through an existing peripheral intravenous line without the need for additional needle sticks.

While the apparatus 7000 described above with reference to FIGS. 15-22 includes an introducer 7100 with a first member 7150 and a second member 7160, in some embodiments, an apparatus can include an introducer with any suitable number of portions or members. For example, FIGS. 23 and 24 illustrate an apparatus 8000 according to an embodiment. The apparatus 8000 includes at least an introducer 8100 and a cannula or catheter 8200 and is configured to be moved between a first configuration (FIG. 23) and a second configuration (FIG. 24).

The introducer 8100 includes a first member 8150, a second member 8160, and a third member 8170. In some embodiments, the first member 8150 can have a first diameter, the second member 8160 can have a second diameter, larger than the first diameter, and the third member 8170 can have a third diameter, larger than the second diameter. In this manner, at least a portion of the first member 8150 can be movably disposed within the second member 8160. Similarly, at least a portion of the second member 8160 can be movably disposed within the third member 8170. In this manner, the introducer 8100 can be configured to be moved in a telescopic motion, as similarly described above with respect to the introducer 7100.

As shown in FIGS. 23 and 24, the first member 8150 includes a set of protrusions 8156 disposed at a proximal end 8151 and a distal end 8152 of the first member 8150. The second member 8160 similarly includes a set of protrusions 8161 and a set of grooves 8161 disposed at a proximal end 8161 and a distal end 8162 of the second member 8160. In a similar manner, the third member 8170 includes a set of grooves 8171 disposed at a proximal end 8171 and a distal end 8172 of the third member 8170. The set of protrusions 8156 and 8166 are configured to selectively engage the set of grooves 8167 and 8177, respectively, as described in further detail herein.

The introducer 8100 includes a proximal end 8120 and a distal end 8130. The proximal end 8120 is configured to receive a portion of the catheter 8200. More specifically, the catheter 8200 is movably disposed within the introducer 8100 such that a proximal end 8220 extends through the proximal end 8120 of the introducer 8100. The distal end 8130 of the introducer 8100 is coupled to a lock mechanism 8131. The lock mechanism 8131 can be any suitable lock mechanism described herein. Therefore, the lock mechanism 8131 is not described in further detail.

The catheter 8200 includes the proximal end 8220 and a distal end 8230. As described above, the proximal end 8220 is configured to extend through the proximal end 8120 of the introducer 8100 when the catheter 8200 is disposed within the introducer 8100. The proximal end 8220 is coupled to a lock mechanism 8221. The lock mechanism 8221 is further coupled to a needle 8222 and a sheath 8223. The lock mechanism 8221, the needle 822, and the sheath 8223 can be substantially similar in form and function to the lock mechanism 2221, the needle 2222, and the sheath 2223, respectively, described above with reference to FIG. 3. Therefore, the lock mechanism 8221, the needle 8222 and the sheath 8223 are not further described herein.

As shown in FIG. 23, the apparatus 8000 can be in the first configuration such that the introducer 8100 is in a non-collapsed configuration. Similarly stated, the third member 8170 of the introducer 8100 is in a proximal position, relative to the second member 8160, and the second member 8160 is in a proximal position, relative to the first member 8150. Expanding further, in the first configuration, the grooves 8167 disposed at the distal end 8162 of the second member 8160 are in contact with the protrusions 8156 disposed at the proximal end 8151 of the first member 8150. Similarly, the grooves 8177 disposed at the distal end 8172 of the third member 8170 are in contact with the protrusions 8166 disposed at the proximal end 8161 of the second member 8160. The arrangement of the protrusions 8156 and 8166 within the grooves 8167 and 8177, respectively, is such that the introducer 8100 is maintained in the non-collapsed (e.g., extended or telescoped configuration). Furthermore, the protrusions 8156 and 8166 can form a friction fit with a surface defining the grooves 8167 and 8177. In this manner, the introducer 8100 can be maintained within the first configuration until an external force is applied to the introducer 8100 to move the introducer towards the second configuration.

For example in use, a user (e.g., a phlebotomist) can engage the introducer 8100 and apply a given force, as indicated by the arrow JJ in FIG. 24. In this manner, the applied force can be such that the third member 8170 moves in the distal direction relative to the second member 8160. Similarly, the second member 8160 is moved in the distal direction relative to the first member 8150 (e.g., the applied force is sufficiently large to overcome the friction force between the protrusions 8156 and 8166 and the surface defining the grooves 8167 and 8177, respectively). Therefore, the introducer 8100 is moved to the second configuration in which the introducer 8100 is substantially collapsed or compressed. Furthermore, the relative distal movement of the third member 8170 and the second member 8160 is such that the set of grooves 8167 at the proximal end 8161 and the distal end 8162 of the second member 8160 engage the set of protrusions 8156 at the proximal end 8151 and the distal end 8152, respectively, of the first member 8150. Similarly, the set of grooves 8177 at the proximal end 8171 and the distal end 8172 of the third member 8170 engage the set of protrusions 8166 at the proximal end 8161 and the distal end 8162 of the second member 8160.

In this manner, the introducer 8100 is in the second configuration and the set of protrusions 8156 and 8166 engage the surfaces defining the set of grooves 8167 and 8177 to define a friction fit. Thus, the introducer 8100 is maintained in the second configuration. Furthermore, the telescopic motion of the introducer 8100 is such that the catheter 8200 disposed within the introducer 8200 is advanced through the lock mechanism 8131, as shown in FIG. 24. As described herein, the lock mechanism 8131 can be coupled to any suitable adapter and/or peripheral intravenous line. Therefore, when in the second configuration, the catheter 8200 extends beyond the PIV to draw a portion of a bodily fluid, as described herein (e.g., similar to the apparatus 7000 described herein with reference to FIGS. 15-22).

Figure 25:
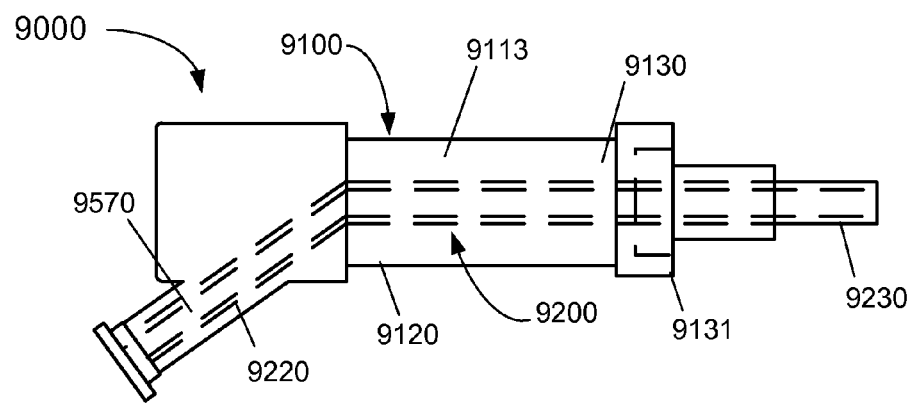
FIGS. 25 and 26 are schematic illustrations of an apparatus in a first configuration and a second configuration, according to an embodiment.
Figure 26:
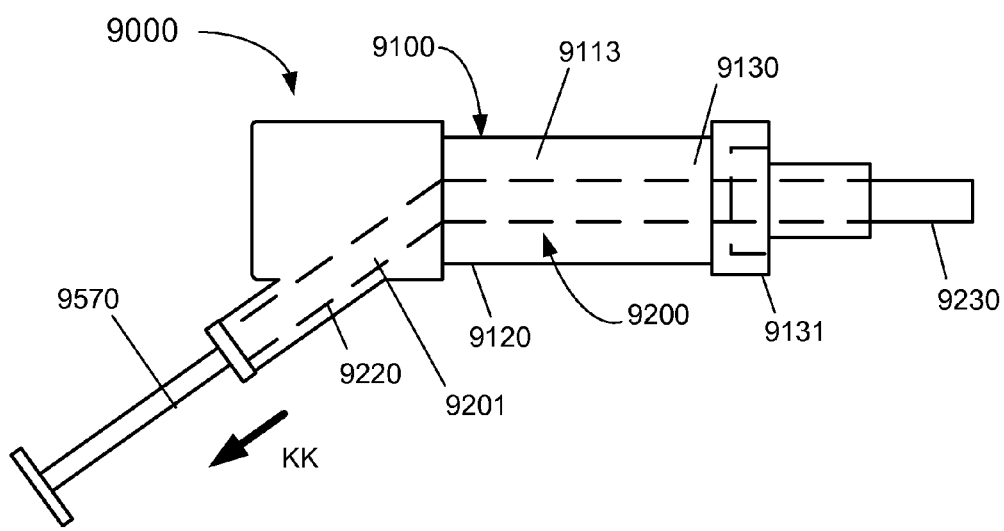

While the apparatus 6000 described above with reference to FIGS. 9-14 includes an annular shaped actuator 6500, in some embodiments, an apparatus can include any suitable actuator. For example, FIGS. 25 and 26 illustrate an apparatus 9000 according to an embodiment, in a first configuration and a second configuration, respectively. The apparatus 9000 includes an introducer 9100, a cannula 9200, and an actuator 9570. The introducer 9100 includes a proximal end 9120 and a distal end 9230 and defines a lumen 9113. The distal end 9230 is configured to be coupled to a lock mechanism 9131. The cannula 9200 includes a proximal end 9220 and a distal end 9230 and defines a lumen 9201. The introducer 9100 and the cannula 9200 can be substantially similar in form and function to any introducer and cannula/catheter described herein. Therefore, the introducer 9100 and the cannula 9200 are not described in further detail herein.

As shown in FIG. 25, the actuator 9570 can be configured to be a stylet or wire. In this manner, the actuator 9570 can be movably disposed within the cannula 9200. Furthermore, the actuator 9570 can be sufficiently stiff such as to advance the cannula 9200 through the introducer 9100, the lock mechanism 9131, and an existing PIV (not shown in FIGS. 25 and 26) substantially without kinking or creasing. The actuator 9570 can be configured to be moved in the proximal direction relative to the cannula 9200, as indicated by the arrow KK in FIG. 26. In this manner, the actuator 9570 can be removed from the cannula 9200 and the cannula 9200 can be placed in fluid communication with a fluid container. Thus, the cannula 9200 can facilitate a transfer of a bodily fluid from a patient to the fluid container, as described above.

Figure 27:
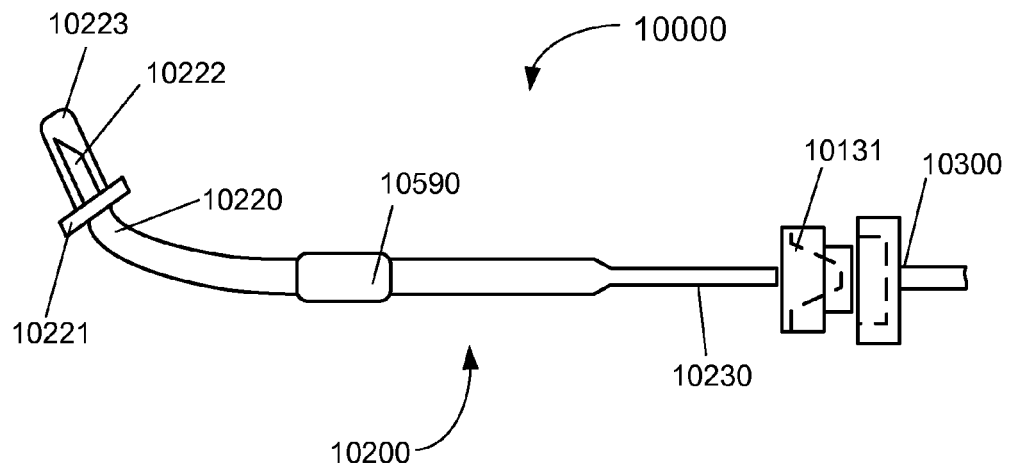
FIGS. 27 and 28 are schematic illustrations of an apparatus in a first configuration and a second configuration, according to an embodiment.
Figure 28:
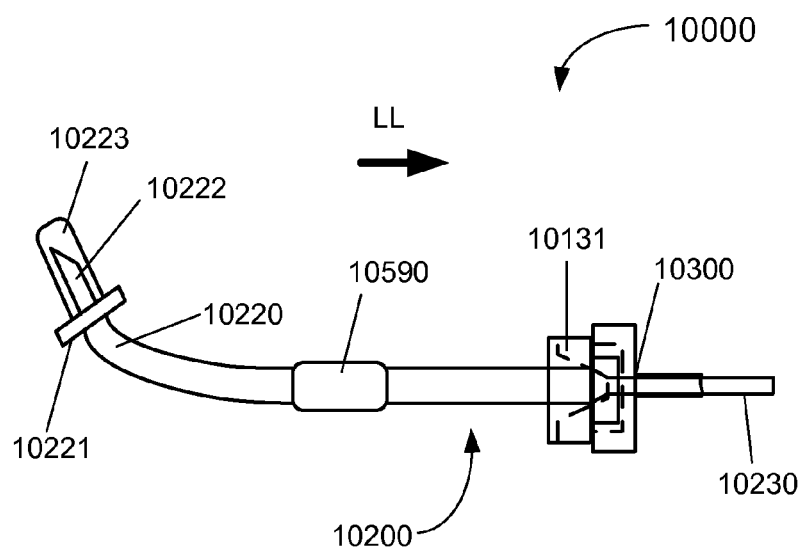

While the embodiments described herein have included an introducer, in some embodiments, an apparatus need not include an introducer. For example, FIGS. 27 and 28 illustrate an apparatus 10000 according to an embodiment, in a first configuration and a second configuration, respectively. The apparatus 10000 can include a cannula or catheter 10200 with a proximal end 10220 and a distal end 10230. The cannula 10200 can be substantially similar in form and function to any cannula/catheter described herein. For example, in some embodiments, the proximal end 10220 includes a lock mechanism 10221, a needle 10222, and a sheath 10223, substantially similar to the lock mechanism 2221, the needle 2222, and the sheath 2223 described above with respect to FIG. 3.

The catheter 10200 is coupled to a handle 10590 configured to be engaged by a user (e.g., a phlebotomist). The apparatus 10000 can further include a lock mechanism 10131. The lock mechanism 10131 can be substantially similar in form and function to the lock mechanism 6131 described above with reference to FIG. 11. Therefore, in use, a user can couple the lock mechanism 10131 to a peripheral intravenous line (PIV) 10300 and define a fluid tight seal. With the lock mechanism 10131 coupled to the PIV 10300, the user can engage the handle 10590 coupled the catheter 10200 to advance the catheter 10200 through the lock mechanism 10131 and the PIV 10300, as indicated by the arrow LL in FIG. 28. Thus, the catheter 10200 can be placed in fluid communication with a fluid container and with the catheter 10200 extended beyond the PIV 10300, the catheter 10200 can facilitate a transfer of a bodily fluid from a patient to the fluid container, as described above.

Figure 29:
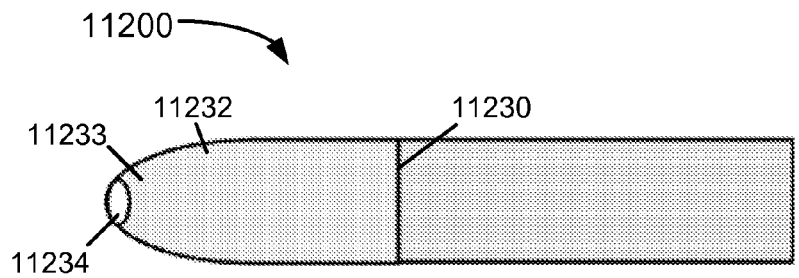
FIGS. 29-37 are side views of various catheter configurations included in an apparatus, according to an embodiment.

While specific cannulas or catheters are described herein as including a distal end of a particular configuration (i.e., with circumferential openings, etc.), in some embodiments the distal end of the catheter or cannula can include a different structure configured to facilitate the drawing of blood through the catheter. For example, FIG. 29 illustrates a catheter 11200 that includes a distal end 11230 with a bullet-shaped tip 11232. The bullet-shaped tip 11232 includes an end portion 11233 that defines a single opening 11234 at a distal end surface of the bullet-shaped tip.

Figure 30:
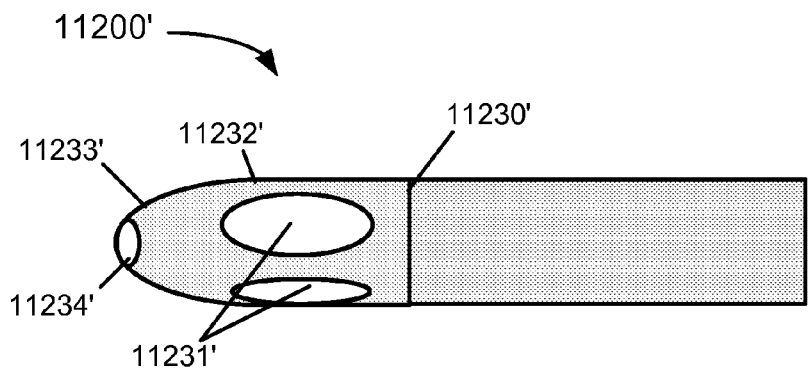

In some embodiments, such as, for example, a catheter 11200' shown in FIG. 30, a bullet-shaped tip 11232' includes an end portion 11233' that defines an end opening 11234'. In such embodiments, the bullet-shaped tip 11232' includes a set of side-wall openings 11231'. The end opening 11234' and the side openings 11231' can be configured to produce a laminar flow and act to transport a bodily fluid (i.e., blood) to a volume outside the catheter 11200'. While the openings 11231, 11231', 11234, and 11234' are illustrated as having a particular configuration, the shape and orientation/relative position of the openings can be varied to facilitate the fluid flow through the catheter.

Figure 31:
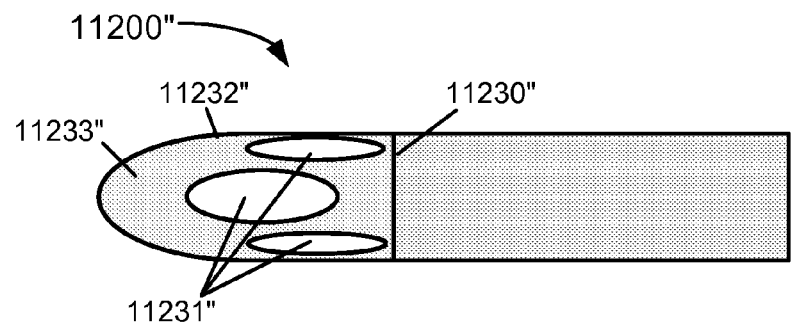

As shown in FIG. 31 the bullet-shaped tip 11232" can be configured to include a substantially closed rounded end portion 11233". In this manner, the bullet-shaped tip 11232" can be used to move through clots existing within a peripheral intravenous line. The bullet-shaped tip 11232" includes a set of side-wall openings 11231" that are operative to transport a bodily fluid (i.e., blood) to a volume outside the catheter 11200".

Figure 32:
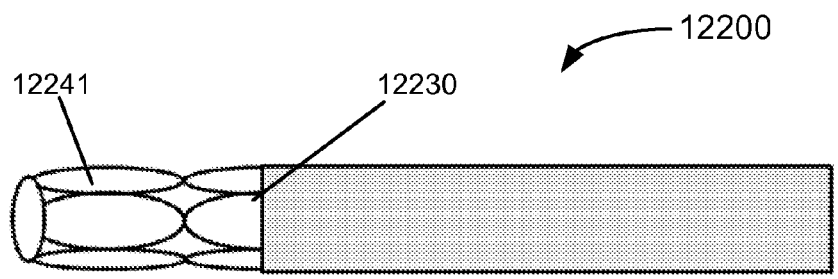
Figure 33:
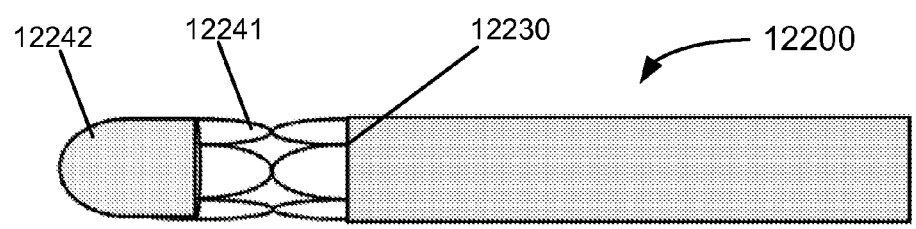
Figure 34:
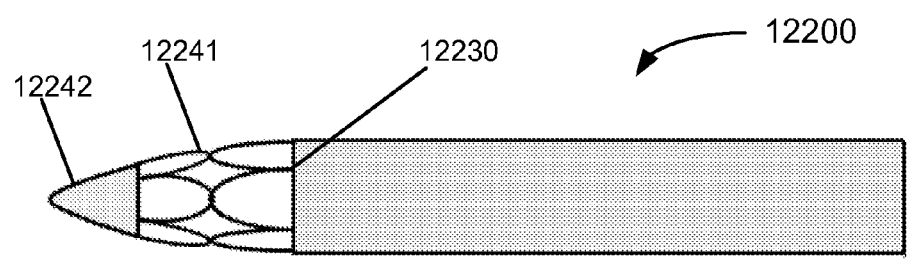

In some embodiments, for example those shown in FIGS. 32-34, a catheter 12200 includes a distal end 12230 with a wireframe tip 12241 having a stent-like configuration. The wireframe tip 12241 can be a flexible mesh configured to extend away from the distal end 12230 of the catheter 12200. The wireframe tip 12241 can act to transport a bodily flow (i.e., blood) to a volume outside the catheter 12200. In some embodiments, the wireframe tip 12241 can include a capped end 12242. The capped end 12242 can be any suitable size, shape, or configuration and, in some embodiments, can include any suitable number of openings.

Figure 35:
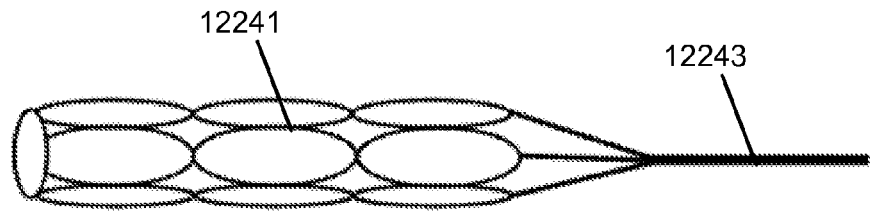
Figure 36:
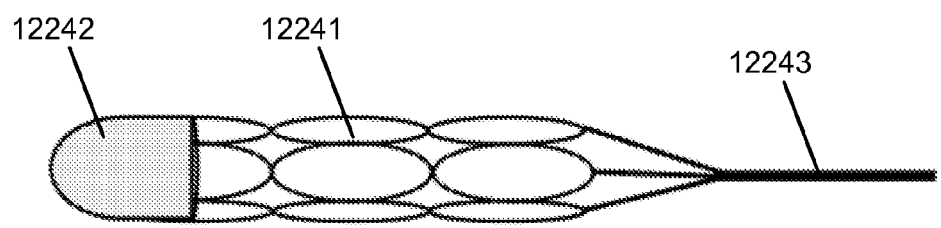
Figure 37:
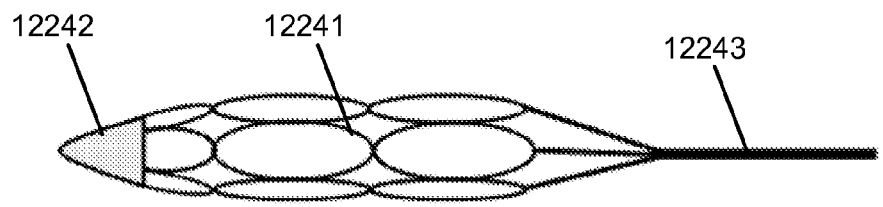
Figure 38:
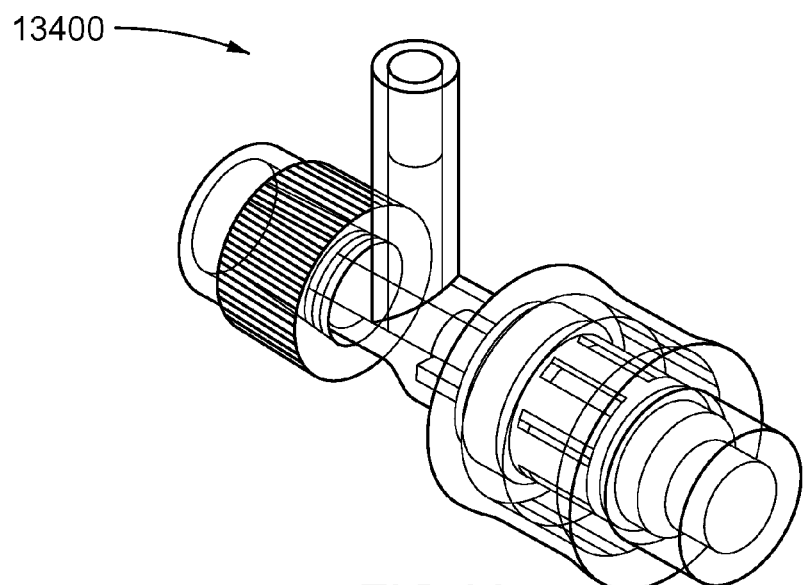
FIGS. 38-43 are various views of two-port adapters, according to various embodiments.
Figure 39:
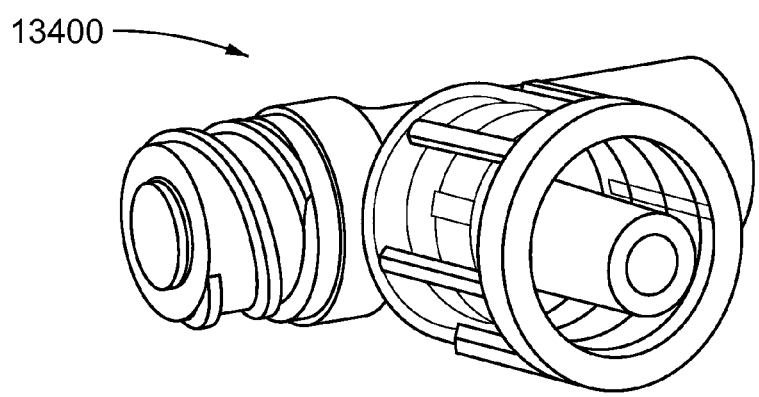
Figure 40:
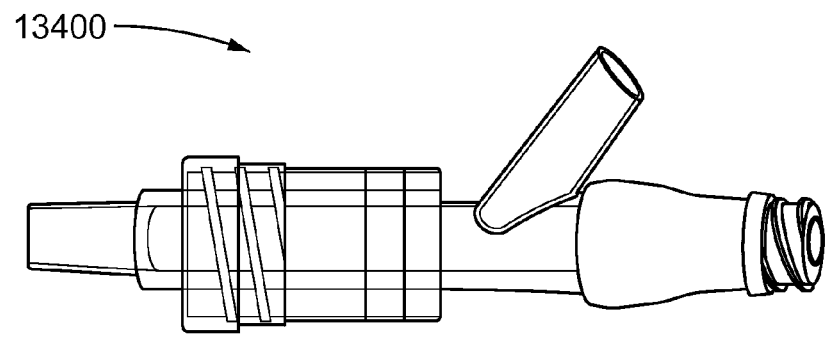
Figure 41:
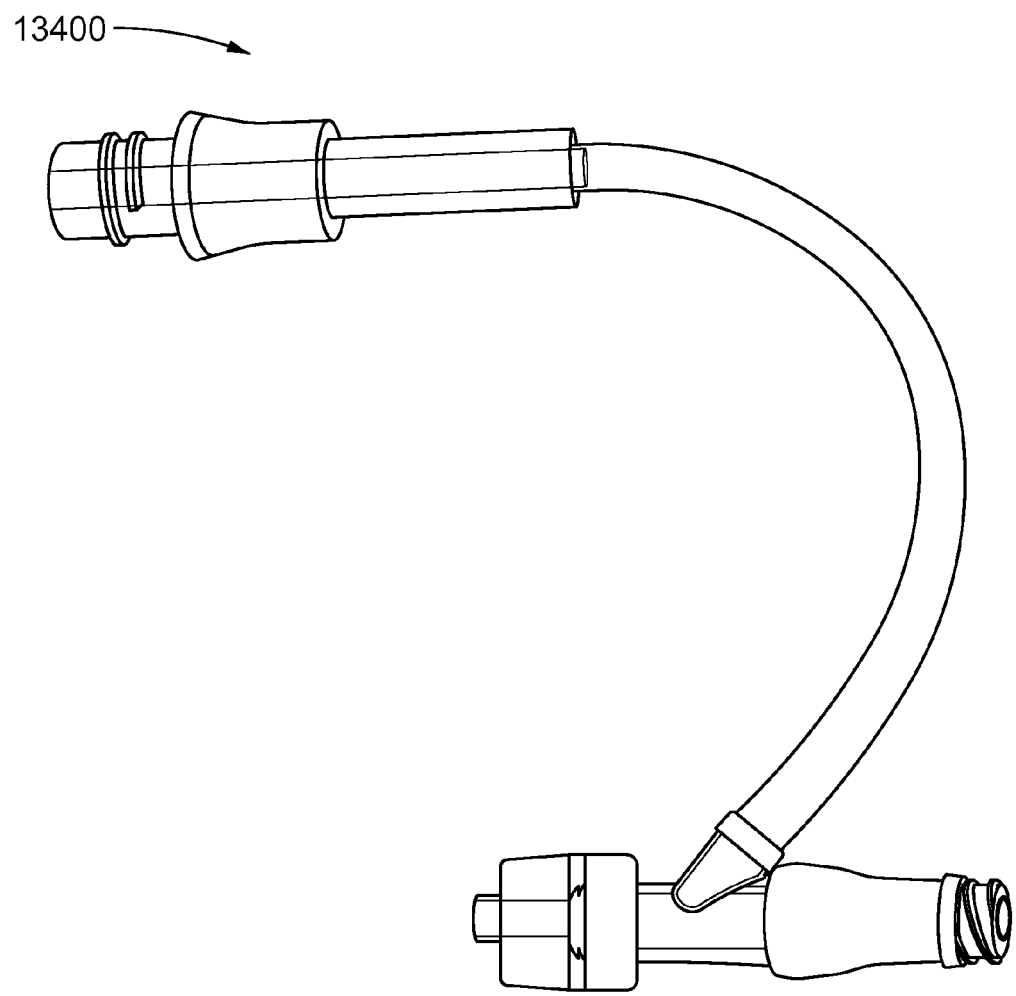
Figure 42:
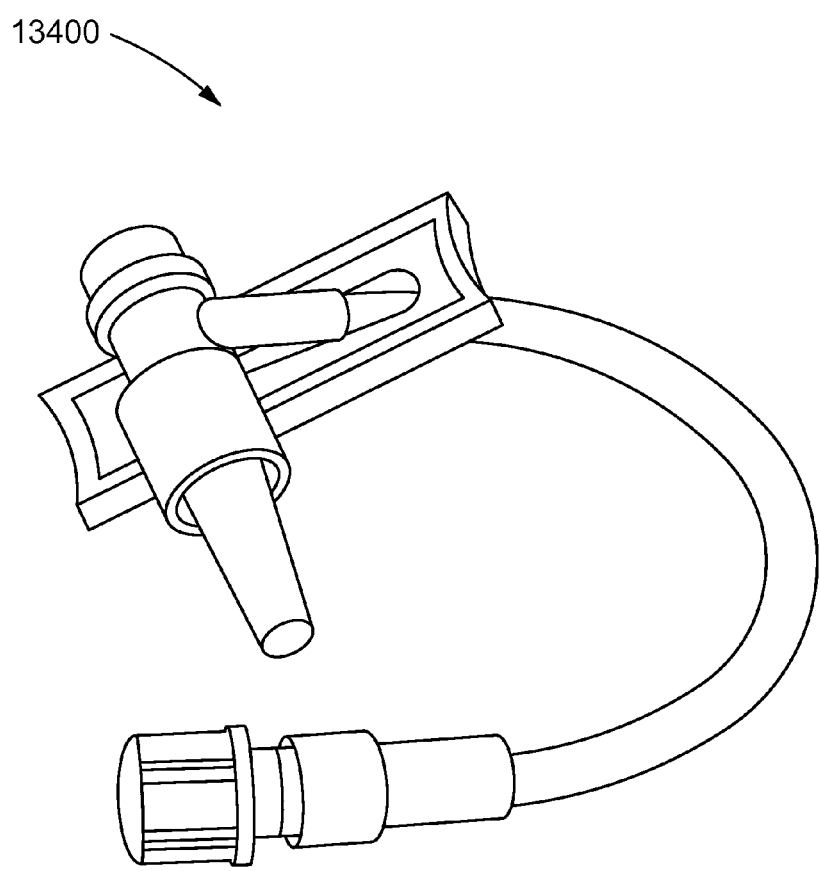
Figure 43:
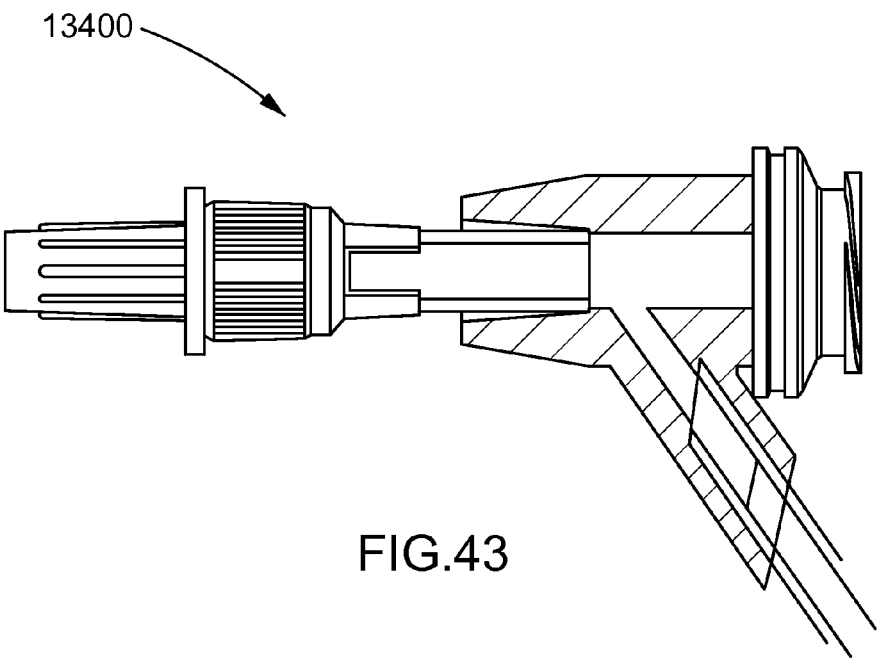

In some embodiments, the wireframe tip 12241 can be connected to a guide wire 12243 and used without an additional catheter, as shown in FIGS. 35-37. Similarly stated, the wireframe tip 12241 can be inserted into an existing peripheral intravenous line via a guide wire and without the catheter of FIG. 10. In this manner, the wireframe tip 12241 can act as a stent and support the walls of the vein such that blood can be drawn through the existing peripheral intravenous line. In such a configuration, the wireframe tip 12241 can be positioned within the existing peripheral intravenous line at any suitable location. For example, the wireframe tip can be positioned adjacent the distal end of the intravenous line.

As described above with reference to FIGS. 9-14, the blood draw apparatus 6000 can be coupled to the adapter 6400 which is further coupled to the PIV 6300. As stated, the adapter 6400 can be any suitable adapter. For example, in some embodiments, an adapter 13400 can be any of the adapters 13400 shown in FIGS. 38-43. In such embodiments, the adapters 13400 can be dual port adapters such as Y-adapters or T-adapters. In such embodiments, the adapters 13400 can include any suitable locking mechanisms, valves, coupling members, seal members, and/or the like, described herein.

Figure 44:
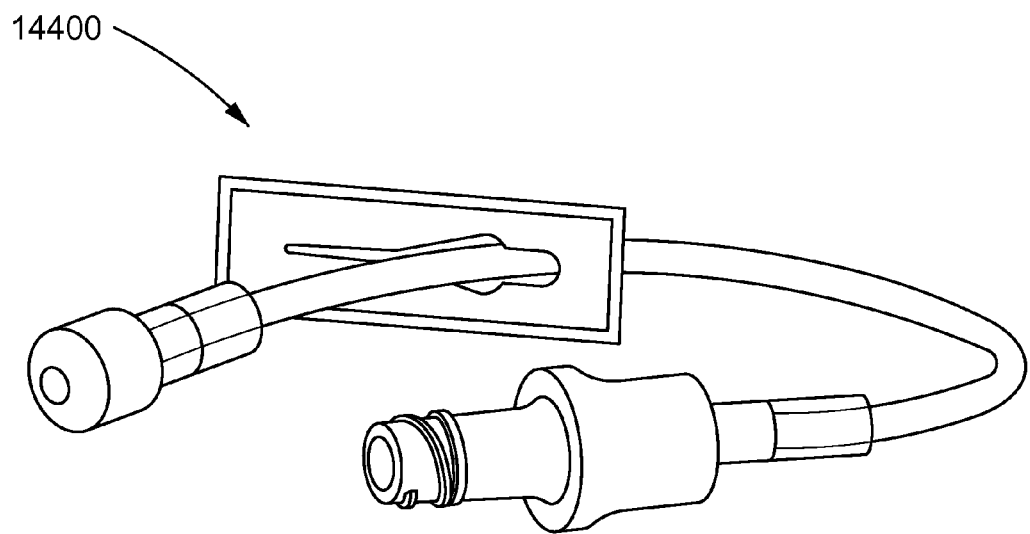
FIGS. 44 and 45 are views of single-port adapters, according to embodiments.
Figure 45:
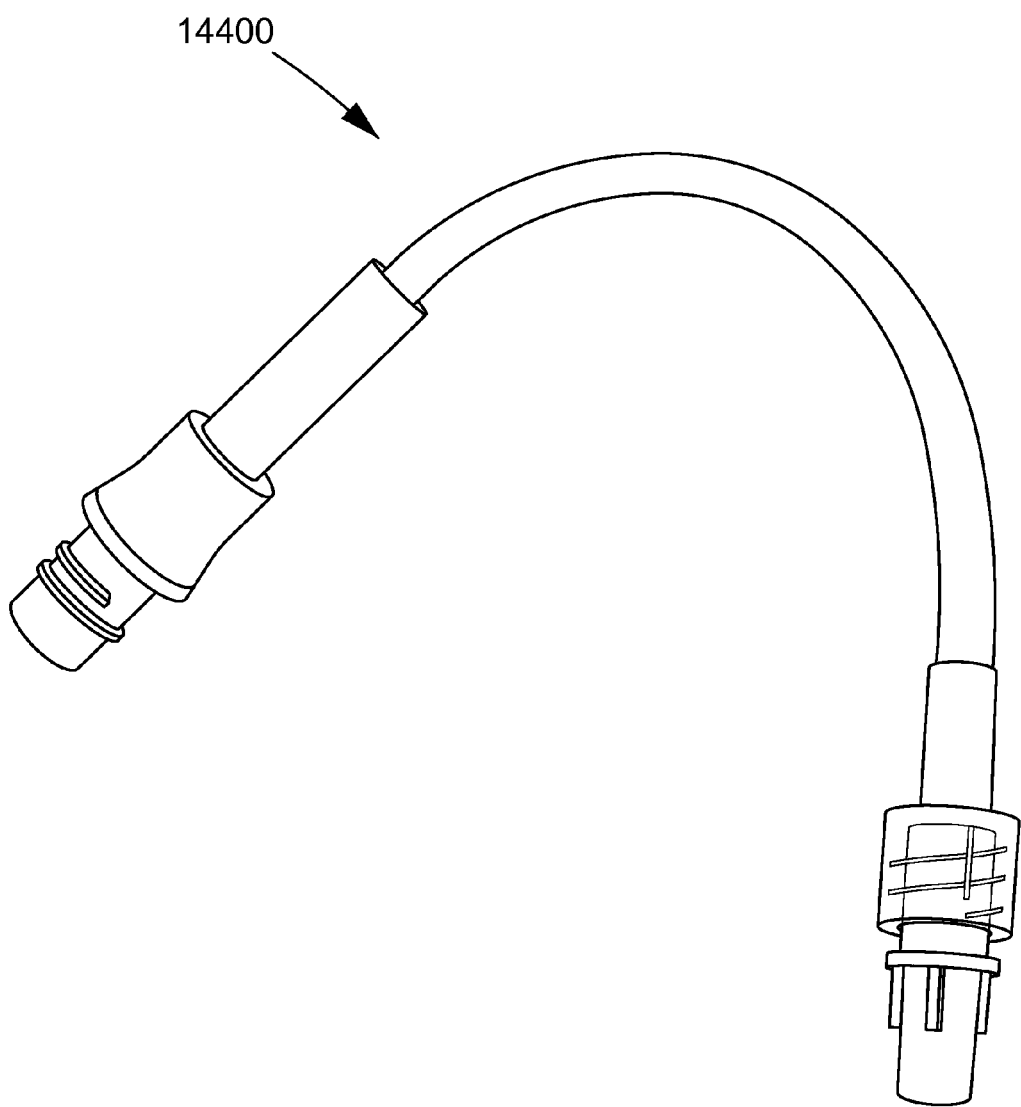

While FIGS. 38-43 illustrate dual port adapters 13400, in some embodiments, an adapter can include a single port. For example, in some embodiments, an adapter 14400 can be either adapter 14400 shown in FIGS. 44 and 45. In such embodiments, the adapter 14400 includes a single port configured to administer a fluid and/or withdraw a fluid to or from the body.

Figure 46:
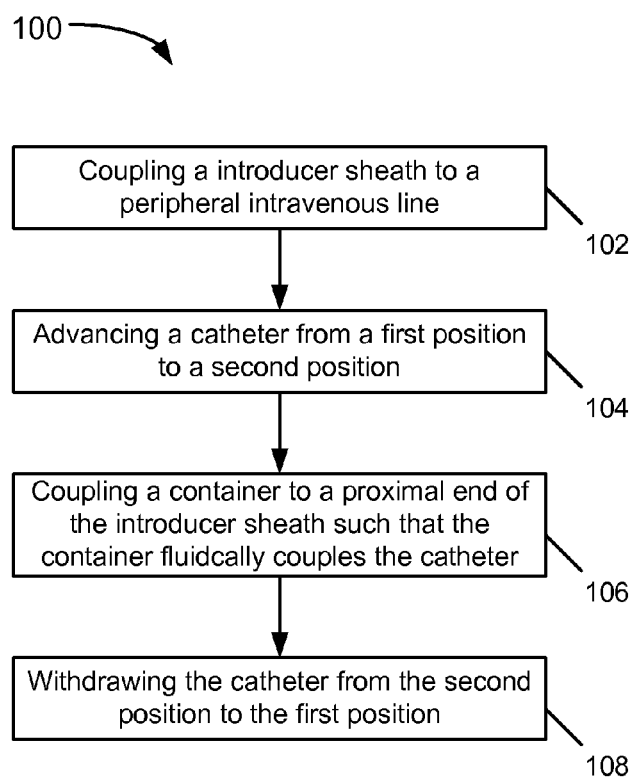
FIG. 46 is a flowchart illustrating a method of phlebotomy through a peripheral intravenous line, according to an embodiment.

FIG. 46 is a flowchart illustrating a method for drawing blood through a peripheral intravenous line. In some embodiments, a method 100 includes coupling an introducer sheath to a peripheral intravenous line (PIV), at 102. For example, in some embodiments, the introducer sheath can include a locking mechanism disposed at a distal end portion configured to engage a known PIV. In this manner, the locking mechanism can physically and fluidically couple at least a portion of the introducer with the PIV. In some embodiments, an adapter is disposed between the PIV and the locking mechanism.

The introducer sheath is configured to house, at least partially, a catheter. The method 100 further includes advancing the catheter from a first position, in which the catheter is substantially within the introducer, to a second position in which the catheter is substantially outside the introducer, at 104. For example, in some embodiments, the catheter is at least operatively coupled to an actuator such that a user can engage the actuator to move the catheter in a distal direction, relative to the introducer. Thus, the catheter moves in the distal direction and can be advanced through the locking mechanism, the adapter (if present), and the PIV. Furthermore, the catheter can be advanced such that a distal end of the catheter extends beyond the PIV and into a portion of a patient (e.g., a vein).

The method 100 includes coupling a container to a proximal end of the introducer sheath such that the container is fluidically coupled to the catheter, at 106. In some embodiments, a proximal end of the catheter includes a needle configured to pierce a portion of a fluid container, such as, for example, a Vacutainer®. In this manner, the catheter is placed in fluid communication with the fluid container. More specifically, with the catheter disposed within, for example, a vein of the patient, the fluid container is placed in fluid communication with the vein. In this manner, a desired amount of a bodily fluid (e.g., blood) can be drawn from the patient and stored in the fluid container.

With the desired amount of bodily fluid collected, the method 100 can include withdrawing the catheter from the second position towards the first position, at 108. In this manner, the catheter can be moved in the proximal direction such that the distal end of the catheter is again disposed within the introducer. With the distal end of the catheter disposed within the introducer, the introducer and/or the locking mechanism can be configured to fluidically isolate the catheter from a volume outside the introducer. Thus, the introducer and catheter can be safely disposed of without concern of spreading fluid borne pathogens.

The components of the blood draw apparatus and the Y-adapter can be packaged together or separately. The Y-adapter can also be sold in a package with other IV dressing materials. In some embodiments, the Y-adapter can remain on the IV as long as the IV is in the patient.

The blood draw apparatus can be used with a variety of peripheral IVs. The apparatus allows efficient blood draw while still maintaining the integrity of the sample. In some embodiments, for example, the apparatus will facilitate 20 ml of blood to be drawn in approximately 1-2 minutes. While extracting blood, the blood flow can be laminar to avoid turbulence in the catheter, thereby minimizing hemolysis.

While the blood draw apparatus can be used in a variety of settings (ER, in-patient, etc.), two examples of scenarios are described herein. In the first scenario, the patient has a single peripheral IV. In the second scenario, which is typically less common, the patient has a dedicated second peripheral IV just for phlebotomy purposes. Only one y-adapter is required per patient, and can be attached for the life of the IV, for example, which is typically 3-4 days. A new blood draw apparatus (e.g., any of those described above) can be used for each blood draw.

The assembly of the blood draw apparatus can be the same in either scenario. First, the apparatus is coupled to the y-adapter. Second, the catheter is advanced through the y-adapter and pushed through the peripheral IV catheter into the patient's vein. Once in the vein, a syringe or a negative pressure collection container/tube (e.g., a Vacutainer® tube) is connected to the rear port and fluidically coupled to the catheter to draw and store blood.

The following scenario is provided by way of example. The nurse or phlebotomist inserts a peripheral IV into a patient's arm. The peripheral IV is inserted following standard guidelines and the y-adapter is attached. When it is time to draw blood, the provider can turn off the IV, if it is on, for approximately 1-5 minutes to allow medicine or IV fluids to disperse from the blood-drawing site. To draw the blood sample, the provider attaches the blood draw apparatus to the blood draw port on the y-adapter, advances the internal catheter through the peripheral IV and into the vein. Next, the provider can attach the negative pressure collection container(s)/tube(s) to the apparatus (i.e., place the tube in fluid communication with the blood draw apparatus) to extract the blood sample. In use, a user can discard, for example, the first 3-6 ml of the fluid or blood sample as "waste" then using the next tube(s) as the intended sample. This "wasting" procedure ensures all of the dead space fluid, like saline or medications, is cleared from the vein, peripheral IV and y-adapter as to not contaminate the testing sample being drawn.

In the scenario in which there is a dedicated peripheral IV line for blood draw purposes, the provider inserts a peripheral IV into one arm to administer medicine and another peripheral IV into the opposite arm specifically for blood drawing purposes. When it is time to draw blood, the provider simply follows the steps mentioned above and there is no need to wait the 1-5 minutes to allow fluid or medicine dispersal as in the first scenario.

Each of the components discussed herein can be monolithically constructed or can be a combination of parts. For example, in reference to FIG. 7, the y-adapter 5400 and the introducer 5100 are coupled using locking mechanisms 5431 and 5131, respectively. The y-adapter 5400 and the introducer 5100 can be the same component, wherein the y-adapter 5400 is an integral part of the introducer 5100 and vice-versa. Other aspects of the apparatus shown and described can be modified to affect the performance of the apparatus. For example, the openings in the set of openings described herein at the distal end of the catheter can be in any arrangement, size shape, and/or number, to create preferable flow conditions through the catheter.

While various embodiments have been described above, it should be understood that they have been presented by way of example only, and not limitation. For example, while the cannula 6200 is shown in FIG. 13A as including the first portion 6205 having the first diameter and the second portion 6210 having the second diameter, in some embodiments, a cannula can include a first portion and a second portion of similar diameter.

Where methods and/or schematics described above indicate certain events and/or flow patterns occurring in certain order, the ordering of certain events and/or flow patterns may be modified. Additionally certain events may be performed concurrently in parallel processes when possible, as well as performed sequentially. While various embodiments have been described as having particular features and/or combinations of components, other embodiments are possible having a combination of any features and/or components from any of embodiments as discussed above.

What is claimed is:

1. An apparatus, comprising:
   a cannula having a proximal end and a distal end and defining a lumen therethrough;
   an introducer having a proximal end and a distal end and defining a lumen therethrough, the introducer configured to receive the cannula therein;
   an actuator operatively coupled to the cannula and configured to move the cannula between a first configuration in which the cannula is substantially within the introducer and a second configuration in which the cannula is substantially outside the introducer; and
   a lock coupled to the distal end of the introducer, the lock configured to couple the introducer to a peripheral intravenous line;
   the cannula being disposed within, and extending past an end of the peripheral intravenous line when in the second configuration.

2. The apparatus of claim 1, further comprising:
   an adapter coupled between the introducer and the peripheral intravenous line.

3. The apparatus of claim 1, further comprising:
   an adapter coupled between the distal end of the introducer and the peripheral intravenous line, the adapter including a first lumen and a second lumen.

4. The apparatus of claim 3, wherein the first lumen has a first diameter and the second lumen has a second diameter, the first diameter being different from the second diameter.

5. The apparatus of claim 3, further comprising a backflow preventer coupled to the adapter adjacent the second lumen.

6. The apparatus of claim 1, wherein the cannula defines a plurality of openings adjacent the distal end of the cannula.

7. The apparatus of claim 1, further comprising a port coupled to the proximal end of the introducer, the port being in fluid communication with the cannula, the port further configured to move bodily fluid to a volume outside the cannula when the catheter is in the second configuration.

8. The apparatus of claim 1, further comprising one of a needle or an access port coupled to the proximal end of the cannula.

9. The apparatus of claim 1, wherein the actuator is movably coupled to the introducer and is fixedly coupled to the cannula.

10. The apparatus of claim 1, wherein the cannula is between 18 gauge and 26 gauge.

11. The apparatus of claim 1, wherein the cannula has a Shore durometer of approximately 20 Shore A to 95 Shore D.

12. The apparatus of claim 1, wherein the cannula is maintained entirely within the introducer when in the first configuration.

13. The apparatus of claim 1, wherein a portion of the cannula extends past the proximal end of the introducer when in the first configuration.

14. A method, comprising:
   coupling an introducer to a peripheral intravenous line, the introducer having a proximal end and a distal end;
   advancing a cannula, using an actuator operatively coupled to the cannula, from a first position inside the introducer and outside the peripheral intravenous line to a second position substantially outside the introducer and inside the peripheral intravenous line, the actuator configured to move from a first actuator position relative to the introducer to a second actuator position relative to the introducer;
   coupling a container to the introducer, the container being fluidically coupled to the cannula; and
   withdrawing the cannula from the second position to the first position by moving the actuator towards the first actuator position.

15. The method of claim 14, further comprising:
   removing the container from the introducer before the withdrawing the cannula.

16. The method of claim 14, wherein the advancing the cannula includes slidably moving the cannula substantially out of the introducer using the actuator coupled to the introducer.

17. The method of claim 14, wherein the cannula is maintained within the introducer when in the first position before the advancing and after the withdrawing.

18. The method of claim 14, wherein the cannula is configured to move bodily fluid to a volume outside the body, the cannula having a plurality of openings defined at a distal end thereof, the plurality of openings being in fluid communication with the container.

19. An apparatus, comprising:
   a cannula having a proximal end and a distal end and defining a lumen therethrough;
   an introducer having a proximal end and a distal end and defining a lumen therethrough, the introducer configured to receive the cannula therein;
   an adapter coupled to the introducer, the adapter having a distal end configured to be coupled to a peripheral intravenous line, the adapter defining a first lumen and a second lumen, the first lumen having a first diameter and being configured to receive the cannula therethrough, the second lumen being orthogonal to the first lumen; and
   an actuator operatively coupled to the cannula and configured to move the cannula between a first configuration and a second configuration, the cannula extending past the distal end of the adaptor in the second configuration.

20. The apparatus of claim 19, wherein the introducer is one of integrally coupled or removably coupled to the adaptor.

21. The apparatus of claim 19, wherein the cannula is configured to be coupled to a fluid collection device.

* * * * *